United States Patent
Giles

(10) Patent No.: US 8,440,968 B2
(45) Date of Patent: May 14, 2013

(54) ION-MOBILITY ANALYSER

(75) Inventor: Kevin Giles, Cheshire (GB)

(73) Assignee: Micromass UK Limited, Manchester (GB)

( * ) Notice: Subject to any disclaimer, the term of this patent is extended or adjusted under 35 U.S.C. 154(b) by 0 days.

(21) Appl. No.: 13/166,882

(22) Filed: Jun. 23, 2011

(65) Prior Publication Data

US 2012/0018631 A1   Jan. 26, 2012

Related U.S. Application Data

(63) Continuation-in-part of application No. 12/917,775, filed on Nov. 2, 2010, which is a continuation of application No. 11/816,221, filed on May 23, 2008, now Pat. No. 7,829,849.

(30) Foreign Application Priority Data

Feb. 14, 2005 (GB) .................................... 0503010

(51) Int. Cl.
  *H01J 49/00* (2006.01)
(52) U.S. Cl.
  USPC ........... 250/292; 250/281; 250/282; 250/283; 250/286; 250/287; 250/288; 250/289; 250/290; 250/291; 250/293
(58) Field of Classification Search .......... 250/281–283, 250/286–293
  See application file for complete search history.

(56) References Cited

U.S. PATENT DOCUMENTS

| | | | |
|---|---|---|---|
| 6,545,268 B1 * | 4/2003 | Verentchikov et al. | 250/287 |
| 6,806,466 B2 | 10/2004 | Guevremont et al. | |
| 6,891,157 B2 | 5/2005 | Bateman et al. | |
| 7,075,070 B2 | 7/2006 | Lee et al. | |
| 7,176,453 B2 | 2/2007 | Miller et al. | |
| 7,217,921 B2 | 5/2007 | Guevremont et al. | |
| 7,250,306 B2 | 7/2007 | Guevremont et al. | |
| 7,279,680 B2 | 10/2007 | Miller et al. | |
| 7,417,225 B2 | 8/2008 | Guevremont | |
| 7,714,284 B2 | 5/2010 | Miller et al. | |
| 2003/0150985 A1 * | 8/2003 | Guevremont et al. | 250/287 |
| 2009/0173880 A1 * | 7/2009 | Bateman et al. | 250/292 |
| 2011/0042563 A1 * | 2/2011 | Giles | 250/286 |
| 2011/0042565 A1 * | 2/2011 | Bateman et al. | 250/287 |
| 2011/0095175 A1 | 4/2011 | Bateman | |

FOREIGN PATENT DOCUMENTS

| | | |
|---|---|---|
| JP | 2004529467 | 9/2004 |
| JP | 2003514349 | 3/2009 |

* cited by examiner

*Primary Examiner* — Jack Berman
*Assistant Examiner* — Meenakshi Sahu
(74) *Attorney, Agent, or Firm* — Diederiks & Whitelaw, PLC

(57) ABSTRACT

An ion-mobility analyser is disclosed comprising a plurality of axially segmented upper electrodes, a plurality of axially segmented lower electrodes, a first plurality of axially segmented intermediate electrodes and a second plurality of axially segmented intermediate electrodes which together define an ion pathway. An asymmetric voltage waveform is applied to the upper electrodes and a DC compensating voltage is applied to the lower electrodes in order to separate ions in a vertical radial direction according to their rate of change of ion mobility with electric field strength. At the same time, a DC axial voltage gradient is maintained along the axial length of the analyser in order to separate ions axially according to their ion mobility.

10 Claims, 9 Drawing Sheets

ION-MOBILITY ANALYSER

CROSS REFERENCE TO RELATED APPLICATIONS

This application is a continuation-in-part of U.S. patent application Ser. No. 12/917,755 filed on 2 Nov. 2010 which is a continuation of U.S. patent application Ser. No. 11/816,221 which claims priority to and benefit of U.S. Provisional Patent Application No. 60/657,792 filed on 2 Mar. 2005 and priority to and benefit of United Kingdom Patent Application No. 0503010.1 filed on 14 Feb. 2005. The entire contents of these applications are incorporated herein by reference.

BACKGROUND OF THE INVENTION

The present invention relates to an ion mobility analyser, an ion mobility separator or spectrometer, a method of analysing ions and a method of ion mobility separation or spectrometry.

The mobility K of an ion in a gas under the influence of an electric field E can be considered as being independent of the applied electric field under conditions wherein the energy gained by the ion from the electric field is negligible compared with thermal energies. Such conditions are met when the ratio of the strength of the applied electric field E to the neutral gas number density N of the gas is relatively low. However, if the strength of the electric field is increased or if the neutral gas number density is decreased then the mobility of an ion may then be observed as being dependent upon the ratio of the electric field strength to the neutral gas number density E/N. The mobility of the ion is observed as having a dependence as follows:

$$K\left(\frac{E}{N}\right) = K_0\left[1 + \alpha\left(\frac{E}{N}\right)\right] \quad (1)$$

wherein $K_0$ is the mobility of the ion when the ratio E/N is relatively low and $\alpha(E/N)$ is a function representing the dependence of the mobility of the ion as the strength of the applied electric field increases.

A knowledge of the dependence of the mobility of an ion with electric field strength prompted development of the first differential ion mobility analyser by Buryakov et al. as disclosed in International Journal of Mass Spectrometry and Ion Processes 128 (1993) pp 143-148. The differential ion mobility analyser developed by Buryakov et al. operated by separating ions according to differences in the mobilities of ions under low and high strength electric fields.

The device developed by Buryakov et al. is shown schematically in FIGS. 1A and 1B. The device comprises a pair of parallel electrodes 2a,2b. A flow of gas 5 is arranged to pass between the two electrodes 2a,2b and ions which are to be separated are arranged to be entrained in the flow of gas 5. An asymmetric potential difference or voltage waveform 3 is arranged to be maintained between the electrodes 2a,2b. An asymmetric potential difference or voltage waveform 3 which is applied to the electrodes is shown in FIG. 2 and comprises a relatively high positive voltage $V_{high}$ for a relatively short period of time $T_{high}$ followed by a relatively low negative voltage $V_{low}$ for a relatively long period of time $T_{low}$. The asymmetric potential difference or voltage waveform 3 is arranged such that the product $V_{high} \times T_{high}$ equals the product $V_{low} \times T_{low}$. Consequently, if the mobility of an ion when the electric field is relatively low is the same when the electric field is relatively high then the average trajectory of the ion through the device may be expected to remain substantially parallel to the electrodes 2a,2b. The ion would therefore be expected to be onwardly transmitted through the device as shown in FIG. 1A.

If the mobility of the ion varies with electric field strength then the ion will then be expected to drift towards one or other of the electrodes 2a;2b. The ion will therefore ultimately become lost to the system by hitting one of the electrodes 2a;2b. This is shown in FIG. 1B. However, by applying a DC compensation voltage 4 to one of the electrodes 2a;2b the drift of the ion towards one of the electrodes 2a;2b can be compensated for. By appropriate setting of the DC compensation voltage 4 it is possible to arrange for ions having a specific ion mobility to be onwardly transmitted by the device whereas other ions will drift towards one of the electrodes 2a,2b and will become lost to the system.

Known differential ion mobility analysers do not confine ions within the analyser and therefore operate at atmospheric pressure since at atmospheric pressures the rate of ion diffusion is lower than at sub-atmospheric pressures. Accordingly, the loss of ions as they pass through the ion mobility analyser is minimized. If the gas pressure were to be reduced to sub-atmospheric pressures then ion diffusion would then become an important loss mechanism and the ion mobility analyser would suffer from unacceptable losses of ions.

A disadvantage of known ion mobility analysers is that since they need to operate at atmospheric pressures then high voltage RF generators are also required in order to provide an asymmetric voltage waveform which has a high enough peak amplitude in order to be able to generate an asymmetric voltage waveform which can enable high-field mobility effects to be observed.

It is therefore desired to provide an improved ion mobility analyser.

SUMMARY OF THE INVENTION

According to an aspect of the present invention there is provided an ion-mobility analyser comprising:

an upper series of electrodes;

a lower series of electrodes disposed parallel to the upper series of electrodes;

a first plurality of intermediate electrodes disposed between the upper and lower series of electrodes;

a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;

a gas at a sub-ambient pressure in the ion pathway; and a voltage source configured to apply simultaneously both: (i) an asymmetric voltage waveform to at least some of the electrodes so that ions become separated in a radial direction according to their rate of change of ion mobility with electric field strength; and (ii) a symmetric voltage to at least some of the electrodes so that ions become separated in an axial direction according to their ion mobility.

The analyser preferably comprises a combined Field Asymmetric Ion Mobility Spectrometry-Ion Mobility Spectrometry ("FAIMS-IMS") device.

The asymmetric voltage waveform preferably comprises at least a first voltage component $V_{high}$ having a first peak amplitude and at least a second voltage component $V_{low}$ having a second peak amplitude substantially different from the first peak amplitude.

The first voltage component is preferably applied for a first time period $T_{high}$ and the second voltage component is applied for a second time period $T_{low}$ substantially different from the first time period.

The analyser preferably further comprises a DC voltage source arranged and adapted to apply a DC compensation voltage to either the upper series of electrodes and/or to the first plurality of intermediate electrodes and/or to the second plurality of intermediate electrodes and/or to the lower series of electrodes.

According to an embodiment the upper series of electrodes, the lower series of electrodes, the first plurality of intermediate electrodes and the second plurality of intermediate electrodes are disposed linearly in a direction parallel to the ion pathway.

According to an alternative embodiment the upper series of electrodes, the lower series of electrodes, the first plurality of intermediate electrodes and the second plurality of intermediate electrodes are disposed linearly in a direction orthogonal to the ion pathway.

According to an aspect of the present invention there is provided a method of analysing ions comprising:

providing an ion-mobility analyser comprising an upper series of electrodes, a lower series of electrodes disposed parallel to the upper series of electrodes, a first plurality of intermediate electrodes disposed between the upper and lower series of electrodes, and a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;

providing a gas at a sub-ambient pressure in the ion pathway; and applying simultaneously both: (i) an asymmetric voltage waveform to at least some of the electrodes so that ions become separated in a radial direction according to their rate of change of ion mobility with electric field strength; and (ii) a symmetric voltage to, one or more transient DC voltages to, or a linear axial voltage gradient across at least some of the electrodes so that ions become separated in an axial direction according to their ion mobility.

According to an aspect of the present invention there is provided a multi-mode ion-mobility analyser comprising:

an upper series of electrodes;

a lower series of electrodes disposed parallel to the upper series of electrodes;

a first plurality of intermediate electrodes disposed between the upper and lower series of electrodes;

a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;

a gas at a sub-ambient pressure in the ion pathway; and a voltage source configured to apply a voltage waveform to at least some of the electrodes:

wherein in a first mode of operation either: (i) the voltage source applies simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) the voltage source applies an asymmetric voltage waveform to at least some of electrodes so that ions are separated radially according to their rate of change of ion mobility with electric field strength; or (iii) the voltage source applies a symmetric voltage waveform to, one or more transient DC voltages to, or a linear axial voltage gradient across at least some of electrodes so that ions are separated axially according to their ion mobility; and wherein in a second different mode of operation either: (i) the voltage source applies simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) the voltage source applies an asymmetric voltage waveform to at least some of electrodes so that ions are separated radially according to their rate of change of ion mobility with electric field strength; (iii) the voltage source applies a symmetric voltage waveform to, one or more transient DC voltages to, or a linear axial voltage gradient across at least some of electrodes so that ions are separated axially according to their ion mobility; or (iv) ions are arranged to be transmitted through the analyser without being substantially separated either according to their rate of change of ion mobility with electric field strength or according to their ion mobility.

According to an aspect of the present invention there is provided a method of analysing ions comprising:

providing a multi-mode ion-mobility analyser comprising an upper series of electrodes, a lower series of electrodes disposed parallel to the upper series of electrodes, a first plurality of intermediate electrodes disposed between the upper and lower series of electrodes, a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser; and providing a gas at a sub-ambient pressure in the ion pathway; and wherein in a first mode of operation the method further comprises either: (i) applying simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) applying an asymmetric voltage waveform to at least some of electrodes so that ions are separated radially according to their rate of change of ion mobility with electric field strength; or (iii) applying a symmetric voltage waveform to, one or more transient DC voltages to, or a linear axial voltage gradient across at least some of electrodes so that ions are separated axially according to their ion mobility; and wherein in a second different mode of operation the method further comprises either: (i) applying simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) applying an asymmetric voltage waveform to at least some of electrodes so that ions are separated radially according to their rate of change of ion mobility with electric field strength; (iii) applying a symmetric voltage waveform to, or one or more transient DC voltages to, or a linear axial voltage gradient across at least some of electrodes so that ions are separated axially according to their ion mobility; or (iv) arranging for ions to be transmitted through the analyser without being substantially separated either according to their rate of change of ion mobility with electric field strength or according to their ion mobility.

According to an arrangement there is provided an ion mobility separator or spectrometer which is arranged and adapted to be switched in use between at least two different modes of operation, wherein the ion mobility separator or spectrometer comprises:

one or more first electrodes;

one or more second electrodes;

one or more layers of intermediate electrodes arranged generally or substantially in a plane in which ions travel in use, the one or more layers of intermediate electrodes being arranged between the one or more first electrodes and the one or more second electrodes; and a first voltage device arranged and adapted to apply one or more voltage waveforms to the one or more first electrodes and/or to the one or more layers of intermediate electrodes and/or to the one or more second electrodes;

wherein in a first mode of operation the ion mobility separator or spectrometer is arranged and adapted to separate ions according to differences or changes of their ion mobility with electric field strength wherein the first voltage device is arranged and adapted to apply a first voltage waveform to the one or more first electrodes and/or to the one or more layers of intermediate electrodes and/or to the one or more second electrodes; and wherein in a second different mode of operation the ion mobility separator or spectrometer is arranged and adapted to separate ions according to their ion mobility wherein the first voltage device is arranged and adapted to apply a second different voltage waveform to the one or more first electrodes and/or to the one or more layers of intermediate electrodes and/or to the one or more second electrodes.

In the first mode of operation the ion mobility separator or spectrometer is preferably operated as a Field Asymmetric Ion Mobility Spectrometry ("FAIMS") device.

The first voltage waveform preferably comprises an asymmetric voltage waveform.

In the first mode of operation the first voltage waveform preferably comprises at least a first voltage component $V_{high}$ having a first peak amplitude and at least a second voltage component $V_{low}$ having a second peak amplitude, wherein the first peak amplitude is substantially different to the second peak amplitude.

The first peak amplitude is preferably positive (or negative) and/or the second peak amplitude is preferably positive (or negative), wherein the first peak amplitude and/or the second peak amplitude are selected from the group consisting of: (i) less than −1000 V; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to −90 V; (xi) −90 to −80 V; (xii) −80 to −70 V; (xiii) −70 to −60 V; (xiv) −60 to −50 V; (xv) −50 to −40 V; (xvi) −40 to −30 V; (xvii) −30 to −20 V; (xviii) −20 to −10 V; (xix) −10 to 0 V; (xx) 0 to 10 V; (xxi) 10 to 20 V; (xxii) 20 to 30 V; (xxiii) 30 to 40 V; (xiv) 40 to 50 V; (xxv) 50 to 60 V; (xxvi) 60 to 70 V; (xxvii) 70 to 80 V; (xxviii) 80 to 90 V; (xxix) 90 to 100 V; (xxx) 100 to 200 V; (xxxi) 200 to 300 V; (xxxii) 300 to 400 V; (xxxiii) 400 to 500 V; (xxxiv) 500 to 600 V; (xxxv) 600 to 700 V; (xxxvi) 700 to 800 V; (xxxvii) 800 to 900 V; (xxxviii) 900 to 1000 V; and (xxxix) more than 1000 V.

The first voltage component is preferably applied or present for a first time period $T_{high}$ and wherein the second voltage component is preferably applied or present for a second time period $T_{low}$, wherein the first time period $T_{high}$ is shorter, longer or substantially the same as the second time period $T_{low}$.

The first time period $T_{high}$ and/or the second time period $T_{low}$ are preferably selected from the group consisting of: (i) <0.1 µs; (ii) 0.1-0.5 µs; (iii) 0.5-1 µs; (iv) 1-2 µs; (v) 2-3 µs; (vi) 3-4 µs; (vii) 4-5 µs; (viii) 5-6 µs; (ix) 6-7 µs; (x) 7-8 µs; (xi) 8-9 µs; (xii) 9-10 µs; (xiii) 10-11 µs; (xiv) 11-12 µs; (xv) 12-13 µs; (xvi) 13-14 µs; (xvii) 14-15 µs; (xviii) 15-16 µs; (xix) 16-17 µs; (xx) 17-18 µs; (xxi) 18-19 µs; (xxii) 19-20 µs; and (xxiii) >20 µs.

The first voltage waveform preferably comprises a waveform selected from the group consisting of: (i) rectangular; (ii) non-rectangular; (iii) curved; (iv) regular; (v) irregular; (vi) stepped; (vii) saw-tooth; and (viii) sinusoidal.

The ion mobility separator preferably comprises a second voltage device arranged and adapted to apply a DC compensation voltage to the upper electrodes and/or to the first and second intermediate electrodes and/or to the lower electrodes, wherein the DC compensation voltage is selected from the group consisting of: (i) less than −1000 V; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to −90 V; (xi) −90 to −80 V; (xii) −80 to −70 V; (xiii) −70 to −60 V; (xiv) −60 to −50 V; (xv) −50 to −40 V; (xvi) −40 to −30 V; (xvii) −30 to −20 V; (xviii) −20 to −10 V; (xix) −10 to 0 V; (xx) 0 to 10 V; (xxi) 10 to 20 V; (xxii) 20 to 30 V; (xxiii) 30 to 40 V; (xiv) 40 to 50 V; (xxv) 50 to 60 V; (xxvi) 60 to 70 V; (xxvii) 70 to 80 V; (xxviii) 80 to 90 V; (xxix) 90 to 100 V; (xxx) 100 to 200 V; (xxxi) 200 to 300 V; (xxxii) 300 to 400 V; (xxxiii) 400 to 500 V; (xxxiv) 500 to 600 V; (xxxv) 600 to 700 V; (xxxvi) 700 to 800 V; (xxxvii) 800 to 900 V; (xxxviii) 900 to 1000 V; and (xxxix) more than 1000 V.

In a mode of operation the second voltage device may be arranged and adapted to sweep, vary, progressively vary or switch the DC compensation voltage applied to the upper electrodes and/or to the intermediate electrodes and/or to the lower electrodes.

The second voltage device may be arranged and adapted to sweep, vary, progressively vary or switch the DC compensation voltage in a generally or substantially stepped, linear, regular, irregular, periodic or non-periodic manner.

In the second mode of operation the ion mobility separator or spectrometer is preferably operated as an Ion Mobility Spectrometer ("IMS") device.

The second voltage waveform preferably comprises a symmetric voltage waveform.

The second voltage waveform is preferably arranged and adapted to urge, propel, force or accelerate at least some ions through and/or along at least a portion of the axial length of the ion mobility separator or spectrometer.

The second voltage waveform may comprise one or more transient DC voltages or potentials or one or more transient DC voltage or potential waveforms which is applied to upper electrodes and/or the lower electrodes and/or the intermediate electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility separator or spectrometer.

The second voltage waveform may comprise one or more substantially constant DC voltages or potentials which is applied to the upper electrodes and/or the lower electrodes and/or the intermediate electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility separator or spectrometer.

The second voltage waveform may less preferably comprise two or more phase-shifted AC or RF voltages which are applied to the upper electrodes and/or the lower electrodes and/or the intermediate electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility separator or spectrometer.

The ion mobility separator or spectrometer preferably comprises a gas phase electrophoresis device or a gas phase ion separator or spectrometer.

The ion mobility separator or spectrometer preferably comprises means arranged so as to provide a stream of gas which flows, in use, through the ion mobility separator or spectrometer and wherein at least some ions are arranged to be onwardly transmitted axially through the ion mobility separator or spectrometer by being entrained in the stream of gas.

According to an embodiment:

(a) the upper electrodes comprise a first array of electrodes and wherein the first array of electrodes comprises at least 2, 3, 4, 5, 6, 7, 8, 9, 10, 11, 12, 13, 14, 15, 16, 17, 18, 19, 20 or more than 20 electrodes; and/or (b) the lower electrodes comprise a second array of electrodes and wherein the second array of electrodes comprises at least 2, 3, 4, 5, 6, 7, 8, 9, 10, 11, 12, 13, 14, 15, 16, 17, 18, 19, 20 or more than 20 electrodes.

The first array of electrodes and/or the second array of electrodes may comprise: (i) a printed circuit board, printed wiring board or etched wiring board; (ii) a plurality of conductive traces applied or laminated onto a non-conductive substrate; (iii) a plurality of copper or metallic electrodes arranged on a substrate; (iv) a screen printed, photoengraved, etched or milled printed circuit board; (v) a plurality of electrodes arranged on a paper substrate impregnated with phenolic resin; (vi) a plurality of electrodes arranged on a fibreglass mat impregnated within an epoxy resin; (vii) a plurality of electrodes arranged on a plastic substrate; or (viii) a plurality of electrodes arranged on a substrate.

According to an embodiment:

(a) at least 5%, 10%, 15%, 20%, 25%, 30%, 35%, 40%, 45%, 50%, 55%, 60%, 65%, 70%, 75%, 80%, 85%, 90%, 95% or 100% of the upper electrodes and/or the lower electrodes have an axial centre to centre spacing selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm; and/or (b) at least 5%, 10%, 15%, 20%, 25%, 30%, 35%, 40%, 45%, 50%, 55%, 60%, 65%, 70%, 75%, 80%, 85%, 90%, 95% or 100% of the upper electrodes and/or the lower electrodes have an axial length selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm; and/or (c) at least 5%, 10%, 15%, 20%, 25%, 30%, 35%, 40%, 45%, 50%, 55%, 60%, 65%, 70%, 75%, 80%, 85%, 90%, 95% or 100% of the upper electrodes and/or the lower electrodes have a width selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm; and/or (d) the upper electrodes and/or the lower electrodes have a thickness selected from the group consisting of: (i) <0.01 mm; (ii) 0.01-0.1 mm; (iii) 0.1-0.2 mm; (iv) 0.2-0.3 mm; (v) 0.3-0.4 mm; (vi) 0.4-0.5 mm; (vii) 0.5-0.6 mm; (viii) 0.6-0.7 mm; (ix) 0.7-0.8 mm; (x) 0.8-0.9 mm; (xi) 0.9-1.0 mm; (xii) 1-2 mm; (xiii) 2-3 mm; (xiv) 3-4 mm; (xv) 4-5 mm; and (xvi) >5 mm; and/or (e) at least 5%, 10%, 15%, 20%, 25%, 30%, 35%, 40%, 45%, 50%, 55%, 60%, 65%, 70%, 75%, 80%, 85%, 90%, 95% or 100% of the upper electrodes and/or the lower electrodes are biased, in use, at a first bias DC voltage or potential with respect to the mean or average voltage or potential of at least some or all of the intermediate electrodes, wherein the first DC bias voltage or potential is selected from the group consisting of: (i) less than −10V; (ii) −9 to −8V; (iii) −8 to −7V; (iv) −7 to −6V; (v) −6 to −5V; (vi) −5 to −4V; (vii) −4 to −3V; (viii) −3 to −2V; (ix) −2 to −1V; (x) −1 to 0V; (xi) 0 to 1V; (xii) 1 to 2V; (xiii) 2 to 3V; (xiv) 3 to 4V; (xv) 4 to 5V; (xvi) 5 to 6V; (xvii) 6 to 7V; (xviii) 7 to 8V; (xix) 8 to 9V; (xx) 9 to 10V; and (xxi) more than 10V; and/or (f) the upper electrodes and/or lower electrodes are supplied in a mode of operation with either: (i) a DC only voltage; (ii) an AC or RF only voltage; or (iii) a DC voltage and an AC or RF voltage.

The one or more layers of intermediate electrodes preferably comprise one or more layers of planar, plate or mesh electrodes.

Each layer of intermediate electrodes preferably comprise one, two or more than two longitudinal electrodes.

At least some or all of the longitudinal electrodes preferably:

(a) have a centre to centre separation in a width direction of the ion mobility separator or spectrometer selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm; and/or (b) have an axial length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; and (xxi) >200 mm; and/or (c) have a width selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm; and/or (d) have a thickness selected from the group consisting of: (i) <0.01 mm; (ii) 0.01-0.1 mm; (iii) 0.1-0.2 mm; (iv) 0.2-0.3 mm; (v) 0.3-0.4 mm; (vi) 0.4-0.5 mm; (vii) 0.5-0.6 mm; (viii) 0.6-0.7 mm; (ix) 0.7-0.8 mm; (x) 0.8-0.9 mm; (xi) 0.9-1.0 mm; (xii) 1-2 mm; (xiii) 2-3 mm; (xiv) 3-4 mm; (xv) 4-5 mm; and (xvi) >5 mm.

The two or more longitudinal electrodes in a layer are preferably substantially co-planar.

The two or more longitudinal electrodes in a layer are preferably supplied, in use, with substantially the same phase of a two-phase or multi-phase AC or RF voltage or signal.

Adjacent or neighbouring layers of longitudinal electrodes are preferably supplied, in use, with substantially opposite or different phases of a two-phase or multi-phase AC or RF voltage or signal and wherein the AC or RF voltage or signal supplied, in use, to the longitudinal electrodes:

(a) has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz; and/or (b) has an amplitude selected from the group consisting of: (i) <50V peak to peak; (ii) 50-100V peak to peak; (iii) 100-150V peak to peak; (iv) 150-200V peak to peak; (v) 200-250V peak to peak; (vi) 250-300V peak to peak; (vii) 300-350V peak to peak; (viii) 350-400V peak to peak; (ix) 400-450V peak to peak; (x) 450-500V peak to peak; and (xi) >500V peak to peak.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the intermediate electrodes are supplied with an AC or RF voltage or signal.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are arranged substantially parallel to one another.

At least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are preferably substantially planar or flat and the ion mobility separator or spectrometer curves in the plane of the electrodes.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are substantially non-planar or non-flat such that the electrodes curve along their axial length.

According to an embodiment:

(a) at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are arranged substantially equidistant from one another; and/or (b) wherein at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are spaced apart from one another by a distance selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

The ion mobility separator or spectrometer may have either a substantially linear, non-linear, regular, non-regular or curved ion guiding region.

The ion mobility separator or spectrometer may have an entrance for receiving ions along a first axis and an exit from which ions emerge from the ion mobility separator or spectrometer along a second axis, wherein the second axis makes an angle θ to the first axis, and wherein θ falls within the range selected from the group consisting of: (i) <10°; (ii) 10-20°; (iii) 20-30°; (iv) 30-40°; (v) 40-50°; (vi) 50-60°; (vii) 60-70°; (viii) 70-80°; (ix) 80-90°; (x) 90-100°; (xi) 100-110°; (xii) 110-120°; (xiii) 120-130°; (xiv) 130-140°; (xv) 140-150°; (xvi) 150-160°; (xvii) 160-170°; (xviii) 170-180°; and (xix) 180°.

The ion mobility separator or spectrometer may comprise an ion guiding region arranged between an ion entrance of the ion mobility separator or spectrometer and an ion exit of the ion mobility separator or spectrometer, and wherein the ion guiding region is substantially linear, non-linear, regular, non-regular, curved, "S"-shaped or has one, two or more than two points of inflexion.

The ion mobility separator or spectrometer may have one, two, three or more than three separate entrances for receiving ions and one, two, three or more than three separate exits from which ions may emerge from the ion mobility separator or spectrometer.

The ion mobility separator or spectrometer preferably has an entrance having a first cross-sectional profile and a first cross-sectional area and an exit having a second cross-sectional profile and a second cross-sectional area.

According to an embodiment:

(a) the first cross-sectional profile is different to the second cross-sectional profile and/or the first cross-sectional area is different to the second cross-sectional area; and/or (b) the first cross-sectional profile and/or the second cross-sectional profile have a substantially circular, oval, rectangular or square cross-section.

The ion mobility separator or spectrometer may be arranged and adapted to be coupled to an ion-optical component selected from the group consisting of: (i) an ion-optical component having a substantially circular, square, rectangular or elliptical cross-sectional profile; (ii) a quadrupole mass filter/analyser having a substantially circular or elliptical cross-sectional profile; (iii) an orthogonal acceleration Time of Flight mass analyser having a substantially square or rectangular cross-sectional profile; (iv) a magnetic sector analyser having a substantially rectangular cross-sectional profile; (v) a Fourier Transform Ion Cyclotron Resonance ("FTICR") mass analyser having a substantially circular or elliptical cross-sectional profile; (vi) a 2D (linear) quadrupole ion trap having a substantially circular or elliptical cross-sectional profile; and (vii) a 3D (Paul) quadrupole ion trap having a substantially circular or elliptical cross-sectional profile.

The ion mobility separator or spectrometer preferably comprises an ion guiding region arranged between an entrance and an exit, and wherein the ion guiding region may either: (i) vary in size and/or shape along the length of the ion guiding region; or (ii) have a width and/or height which progressively tapers or enlarges in size.

According to an embodiment:

(a) the ion mobility separator or spectrometer is maintained, in use, at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >100 mbar; (viii)

>1000 mbar; (ix) 0.0001-0.001 mbar; (x) 0.001-0.01 mbar; (xi) 0.01-0.1 mbar; (xii) 0.1-1 mbar; (xiii) 1-10 mbar; (xiv) 10-100 mbar; and (xv) 100-1000 mbar; or (b) the ion mobility separator or spectrometer is maintained, in use, at a pressure selected from the group consisting of: (i) <0.0001 mbar; (ii) <0.001 mbar; (iii) <0.01 mbar; (iv) <0.1 mbar; (v) <1 mbar; (vi) <10 mbar; (vii) <100 mbar; and (viii) <1000 mbar.

The ion mobility separator or spectrometer may be arranged and adapted to receive a substantially continuous beam of ions and may be arranged and adapted to release or eject ions as a plurality of packets or bunches of ions.

The ion mobility separator or spectrometer may be arranged and adapted to convert a substantially continuous beam of ions into a pulsed or discontinuous beam of ions.

In a mode of operation the ion mobility separator or spectrometer is preferably arranged to operate as an ion guide and to onwardly transmit ions without substantially separating ions according to their mobility.

In a mode of operation the ion mobility separator or spectrometer may be arranged to operate as a collision, fragmentation or reaction device, wherein the collision, fragmentation or reaction device is selected from the group consisting of: (i) a Collision Induced Dissociation ("CID") collision or fragmentation device; (ii) a Surface Induced Dissociation ("SID") fragmentation device; (iii) an Electron Transfer Dissociation fragmentation device; (iv) an Electron Capture Dissociation fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; and (xxviii) an ion-metastable atom reaction device for reacting ions to form adduct or product ions.

The ion mobility spectrometer or separator may further comprise a plurality of insulator layers interspersed or interleaved between the one or more layers of intermediate electrodes, wherein at least 5%, 10%, 15%, 20%, 25%, 30%, 35%, 40%, 45%, 50%, 55%, 60%, 65%, 70%, 75%, 80%, 85%, 90%, 95% or 100% of the one or more layers of intermediate electrodes are arranged on or are deposited on the insulator layers.

According to another aspect of the present invention there is provided a mass spectrometer comprising one or more ion mobility separators or spectrometers as described above.

The mass spectrometer preferably further comprises:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source; and/or (b) one or more mass or mass to charge ratio filters and/or mass analysers arranged upstream and/or downstream of the ion mobility separator or spectrometer, wherein the one or more mass or mass to charge ratio filters and/or mass analysers are selected from the group consisting of: (i) a quadrupole mass filter or analyser; (ii) a Wien filter; (iii) a magnetic sector mass filter or analyser; (iv) a velocity filter; (v) an ion gate; and (vi) an orthogonal acceleration Time of Flight mass analyser; and/or (c) a mass analyser arranged downstream of the ion mobility separator or spectrometer, wherein the mass analyser is selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an axial acceleration Time of Flight mass analyser; and (xiv) an orthogonal acceleration Time of Flight mass analyser; and/or According to another arrangement there is provided a method of ion mobility separation or spectrometry comprising:

providing an ion mobility separator or spectrometer comprising one or more first electrodes, one or more second electrodes and one or more layers of intermediate electrodes arranged generally or substantially in a plane in which ions travel, the one or more layers of intermediate electrodes being arranged between the one or more first electrodes and the one or more second electrodes;

operating the ion mobility separator or spectrometer in a first mode of operation wherein the ion mobility separator or spectrometer separates ions according to differences or changes of their ion mobility with electric field strength wherein a first voltage waveform is applied to the one or more first electrodes and/or to the one or more layers of intermediate electrodes and/or to the one or more second electrodes; and operating the ion mobility separator or spectrometer in a second different mode of operation wherein the ion mobility separator or spectrometer separates ions according to their ion mobility wherein a second different voltage waveform is applied to the one or more first electrodes and/or to the one or more layers of intermediate electrodes and/or to the one or more second electrodes.

According to another aspect of the present invention there is provided a method of mass spectrometry comprising a method as described above.

In a preferred embodiment, the asymmetric voltage waveform is also applied to the one or more layers of intermediate electrodes.

An RF generator may be used to generate the asymmetric voltage waveform and may comprise a relatively low voltage RF generator which preferably provides a voltage waveform having a maximum or peak amplitude of <100V (or >−100 V).

According to an embodiment the device may be operated at a pressure in the range $10^{-2}$ to 100 mbar. According to a particularly preferred embodiment the device may be operated at a pressure in the range $10^{-1}$ to 10 mbar.

Ions are preferably radially confined within the ion mobility spectrometer or separator by an inhomogeneous AC or RF electric field. The inhomogeneous AC or RF electric field is preferably achieved by applying an AC or RF voltage to at least some of the intermediate electrodes so that ions are confined radially within the preferred device.

BRIEF DESCRIPTION OF THE DRAWINGS

Various embodiments of the present invention together with other arrangements given for illustrative purposes only will now be described, by way of example only, and with reference to the accompanying drawings in which.

DETAILED DESCRIPTION OF THE INVENTION

Figure 3:
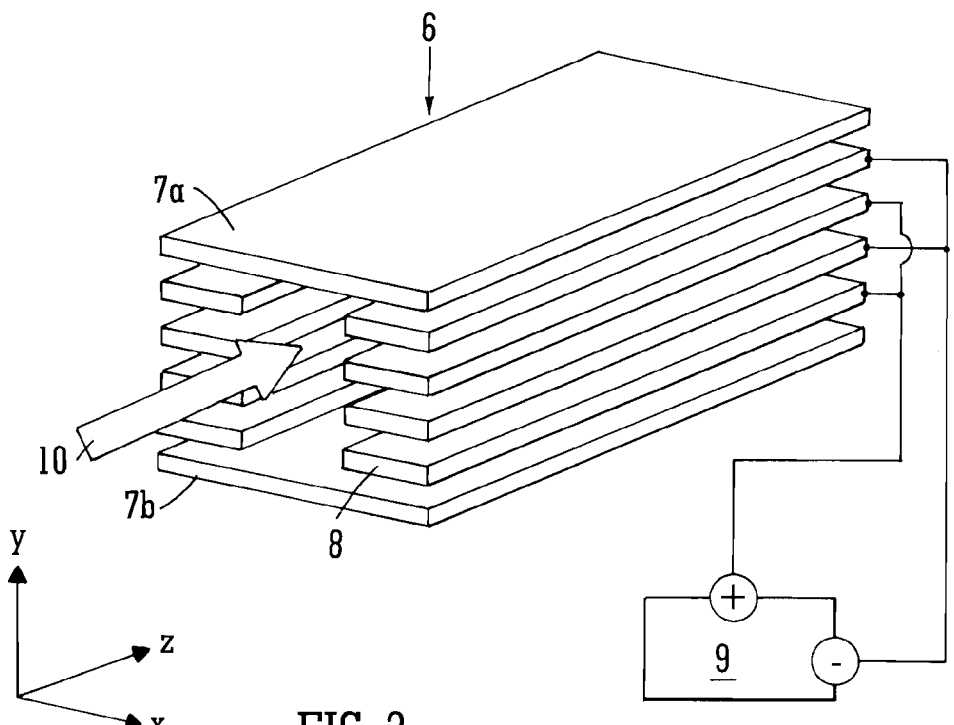
FIG. 3 shows an ion mobility separator or spectrometer.

An ion mobility separator or spectrometer 6 will now be described with reference to FIG. 3. The ion mobility separator or spectrometer 6 comprises an upper electrode 7a, a lower electrode 7b and one or more layers of intermediate electrodes 8. The upper electrode 7a and/or the lower electrode 7b may comprise a planar, plate or mesh electrode. The intermediate electrodes 8 are arranged horizontally between the upper electrode 7a and the lower electrode 7b. The intermediate electrodes 8 comprise one or more planar or plate electrodes. The layers of intermediate electrodes 8 are arranged such that they lie in a plane in which ions travel in use.

Each intermediate layer of electrodes comprises two longitudinal electrodes. The two longitudinal electrodes are horizontally or otherwise separated from each other such that an ion guiding region is provided or formed in between the longitudinal electrodes.

The two longitudinal electrodes in any particular intermediate layer are supplied with the same phase of an AC or RF voltage 9. The longitudinal electrodes in a neighbouring or vertically adjacent intermediate layer are supplied with an opposite phase of the AC or RF voltage 9. The application of an AC or RF voltage 9 to the intermediate or longitudinal electrodes 8 causes ions to be confined in the radial horizontal radial direction (or x-direction) within a pseudo-potential well. The AC or RF voltage 9 which is applied to the intermediate electrodes 8 may have a sinusoidal waveform. However, alternatively the AC or RF voltage may have a non-sinusoidal waveform.

A DC and/or an AC or RF voltage may be applied to the upper electrode 7a and/or to the lower electrode 7b in order to confine ions in the vertical radial direction (or y-direction) within the preferred device 6.

Ion motion in the axial direction (or z-direction) is substantially unimpeded or unaffected by the application of an AC or RF voltage to the intermediate electrodes 8 and by the application of a DC and/or AC or RF voltage to the upper and lower electrodes 7a,7b.

The device 6 can be operated in an ion-guiding only mode of operation wherein an AC or RF voltage is applied to the intermediate electrodes and a DC and/or AC or RF voltage is applied to the upper and lower electrodes 7a,7b. When the device 6 is operated in an ion-guiding only mode of operation an asymmetric voltage waveform is not applied to either the upper electrode 7a or the lower electrode 7b.

When the device 6 operates in an ion guiding only mode of operation the device 6 acts as an ion guide and transmits ions either in the presence of a background neutral gas or in the absence of any such gas. The device 6 can advantageously be operated as an ion guide in an ion guiding only mode of operation at sub-ambient pressures whilst minimising diffusive loss.

According to an embodiment a dual-mode device is provided which can be switched between a first mode of operation wherein the device operates as a differential ion mobility separator or spectrometer and a second mode of operation wherein the ion mobility spectrometer or separator separates ions according to their ion mobility. In the first mode of operation ions are arranged to be separated within the device as a result of ions having an ion mobility at low electric field strengths which differs from the mobility of the ions at high electric field strengths.

In the first mode of operation an asymmetric voltage waveform is applied to either the upper electrode 7a or the lower electrode 7b. According to an embodiment the asymmetric voltage waveform is applied to the upper electrode 7a. Accordingly, an asymmetric potential difference is maintained between the upper electrode 7a and the lower electrode 7b.

Figure 1A:
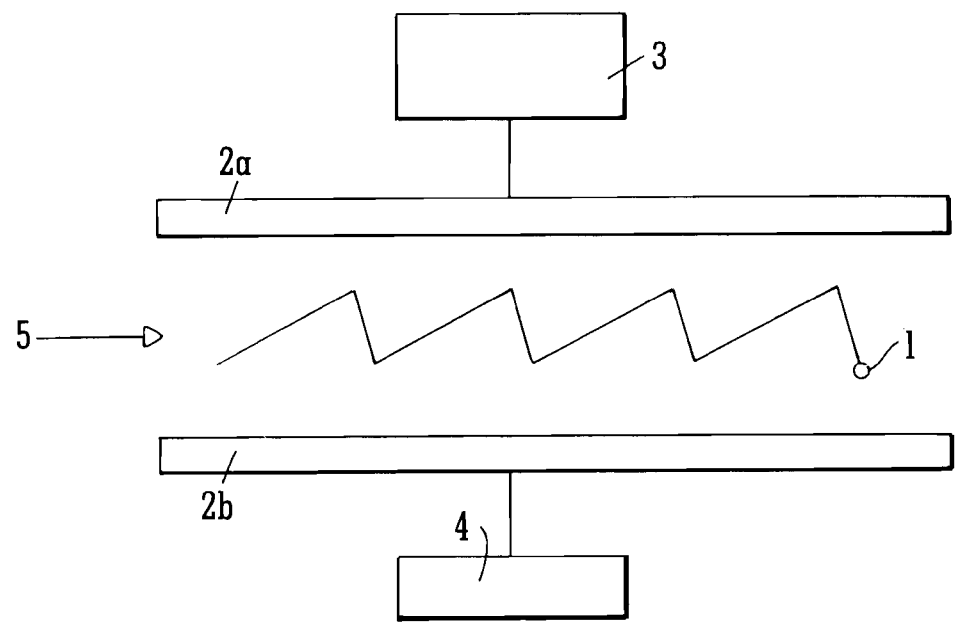
FIG. 1A shows the trajectory of an ion through a known differential ion mobility separator if the mobility of the ion is substantially independent of electric field strength and an asymmetric voltage waveform as shown in FIG. 2 is applied to the upper electrode and FIG. 1B shows the trajectory of an ion through the known differential ion mobility separator if the mobility of the ion exhibits a dependence upon the strength of the applied electric field and an asymmetric voltage waveform as shown in FIG. 2 is applied to the upper electrode.
Figure 1B:
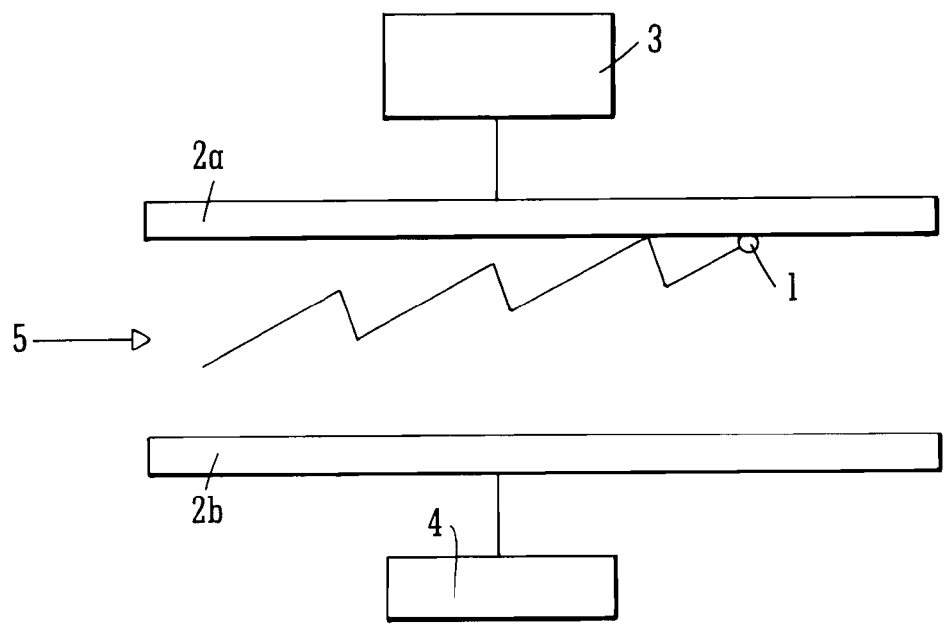
Figure 2:
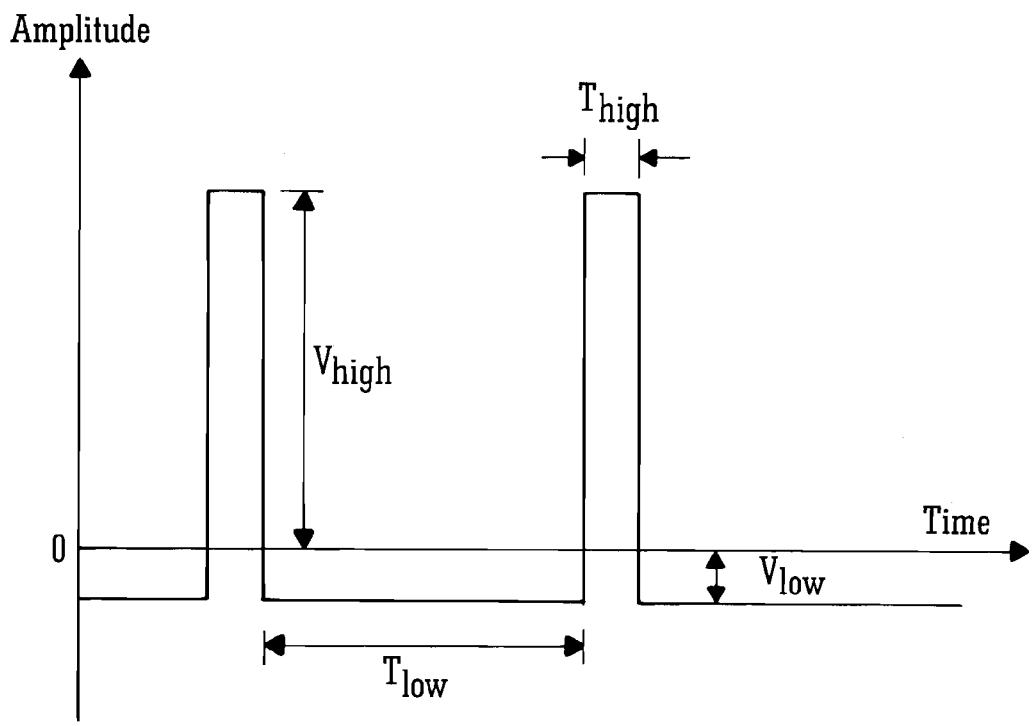
FIG. 2 shows the form of an asymmetric voltage waveform wherein the product $V_{high}*T_{high}$ is arranged to substantially equal the product $V_{low}*T_{low}$.

The asymmetric voltage waveform which is applied to the upper electrode 7a is substantially similar to the asymmetric voltage waveform as shown in FIG. 2 i.e. the product $V_{high}*T_{high}$ is arranged to equal the product $V_{low}*T_{low}$. However, according to other embodiments the asymmetric voltage waveform which is applied to the upper electrode 7a may have a non-rectangular or curved waveform.

The dual-mode ion mobility separator or spectrometer 6 is preferably maintained at sub-ambient gas pressures. Ions are caused to become separated within the device 6 in the vertical radial direction (or y-direction) as the ions pass along and through the device 6. A particular advantage of the device 6 is that the potential or voltage difference between the upper electrode 7a and the lower electrode 7b which is required to be maintained in order to achieve a relatively high ratio of electric field strength E to neutral gas number density N reduces in proportion to the pressure. Therefore, the device 6 can be operated at relatively low pressures but higher order ion mobility effects can nonetheless be observed.

Known differential ion mobility analysers which operate at ambient pressures typically require electric field strengths up to tens of kilovolts per cm in order to separate ions according to differences in the mobility of ions at high and low electric field strengths. However, according to the preferred embodiment the preferred device 6 can be operated at sub-ambient or millibar pressures. As a result the asymmetric voltage waveform which is applied to the device 6 in a first mode of operation may have a much lower electric field strength in the range of tens of volts per cm. Such a relatively low amplitude voltage waveform is still nonetheless sufficient to be able to cause ions to separate according to differences in their ion mobility under high and low electric fields.

Another advantage of the preferred device 6 is that the voltages which are applied to the upper electrode 7a and/or to the lower electrode 7b and/or to the intermediate electrodes 8 may be changed or altered in a rapid manner. As a result the preferred device 6 may be arranged to change mode of operation effectively instantaneously. The preferred device 6 can therefore be switched from operating in one mode of operation to operating in another mode of operation. For example, the preferred device 6 may be switched from operating in a mode of operation wherein an asymmetric voltage waveform is applied to the upper electrode 7a to then operate in a second different mode of operation wherein, for example, a symmetric voltage waveform is applied to the upper electrode 7a and/or to the lower electrode 7b.

In the second mode of operation instead of applying an asymmetric AC or RF voltage waveform to the upper electrode 7a, a static or DC voltage may instead be applied to the upper electrode 7a and/or to the lower electrode 7b. In the second mode of operation the device 6 may be arranged to operate in a mode of operation wherein ions are arranged to be onwardly transmitted without substantially being separated according to differences in their ion mobility as a function of electric field strength. In the second mode of operation ions are separated according to their ion mobility. According to an embodiment the device 6 may be maintained in the second mode of operation at a relatively high pressure and ions may be forced or urged through or along the length of the device 6 by gas flow effects or by other means. For example, an axial DC voltage gradient may be applied along the length of the device 6 in order to cause ions to separate in an axial direction according to their ion mobility.

According to an embodiment an asymmetric voltage waveform may additionally be applied to the longitudinal electrodes or the intermediate electrodes 8. According to this particular embodiment the asymmetric voltage waveform may be arranged so as to be applied to the intermediate electrodes 8 of the device 6 such that the electric field within the device 6 is arranged so as to be substantially constant, uniform or homogenous across at least a portion or substantially the whole of the distance between the upper electrode 7a and the lower electrode 7b at any particular point in time. This is in contrast to the preferred embodiment wherein an inhomogeneous electric field is provided within the device 6 by applying an asymmetric voltage waveform just to the upper electrode 7a.

If a substantially homogenous asymmetric electric field is maintained within the preferred device 6 according to the above described embodiment then the amplitude of the asymmetric voltage waveform which is applied to the longitudinal or intermediate electrodes 8 may be adjusted dependent upon the relative position of the particular electrode between or in relation to the upper electrode 7a and the lower electrode 7b.

Ion motion through the preferred differential ion mobility device 6 in the axial or z-direction direction is preferably perpendicular to the direction of differential ion mobility separation which is in the y-direction. Ions are caused to be transmitted through the preferred device by being contained in a flow of neutral gas 10 which is arranged to be passed through the preferred device 6.

Figure 4:
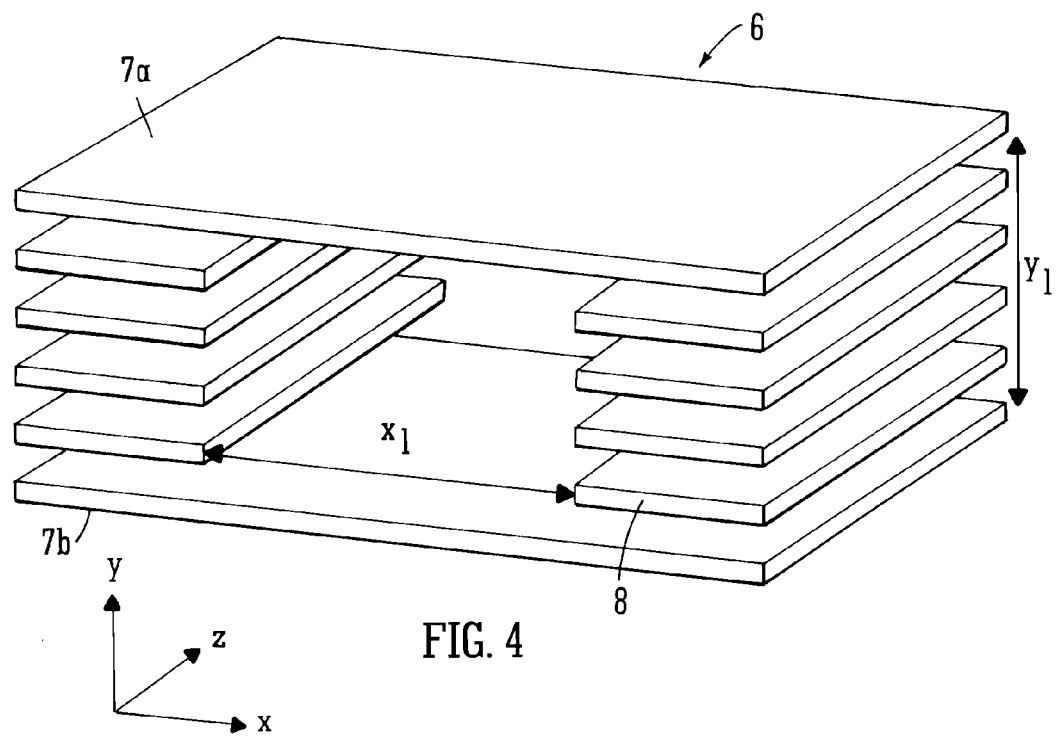
FIG. 4 shows the geometry of an ion mobility separator or spectrometer which was used to model the effects of various electric field conditions upon the trajectories of ions passing through the device.

The effect of applying an asymmetric electric field or voltage waveform to the upper electrode 7a in order to cause ions to become separated according to differences in their mobility as a function of electric field strength was modeled using the SIMION® software package. The particular geometry of the differential ion mobility spectrometer or separator 6 which was used to model the trajectories of ions under various different conditions is shown in FIG. 4. The ion mobility separator or spectrometer 6 was modeled as comprising an upper electrode 7a, a lower electrode 7b and four intermediate layers of electrodes 8. The four intermediate layers of electrodes 8 were provided in between the upper electrode 7a and the lower electrode 7b. Each intermediate layer of electrodes comprised two longitudinal electrodes. The longitudinal electrodes were longer in the axial or z-direction than the width of the electrodes in the x-direction.

The upper electrode 7a, lower electrode 7b and all of the intermediate electrodes 8 were modeled as being 0.5 mm thick (in the y-direction). The upper electrode 7a, lower electrode 7b and all the intermediate electrodes 8 were also modeled as being arranged such that they had a centre-to-centre spacing of 1.5 mm. The face-to-face spacing $y_1$ between the upper electrode 7a and the lower electrode 7b was arranged to be 7.0 mm. The longitudinal electrodes in each intermediate layer 8 were arranged so as to be separated by a distance $x_1$ of 9.8 mm.

The effect of the dependence of the mobility of an ion with electric field strength as described by Eqn. 1 was incorporated into a user program written into the SIMION® model. Following the approach by Lock and Dyer, both the hard sphere and the Langevin collision cross-sections were calculated at each step of the simulation. The larger of the two collision cross-sections was then used as the interaction cross-section in the collision calculations.

At low electric field strengths the Langevin collision cross section (based upon the ion-induced dipole interaction) is largest but decreases with increasing ion velocity (i.e. increasing electric fields) until it falls below the velocity independent hard sphere collision cross section. The drift velocity of an ion at low electric fields (wherein Langevin effects dominates) is proportional to the electric field E. However, at high electric field strengths the drift velocity is proportional to $E^{0.5}$ (wherein Hard Sphere dominates) resulting in a net drift towards either the upper electrode 7a or the lower electrodes 7b.

Figure 5:
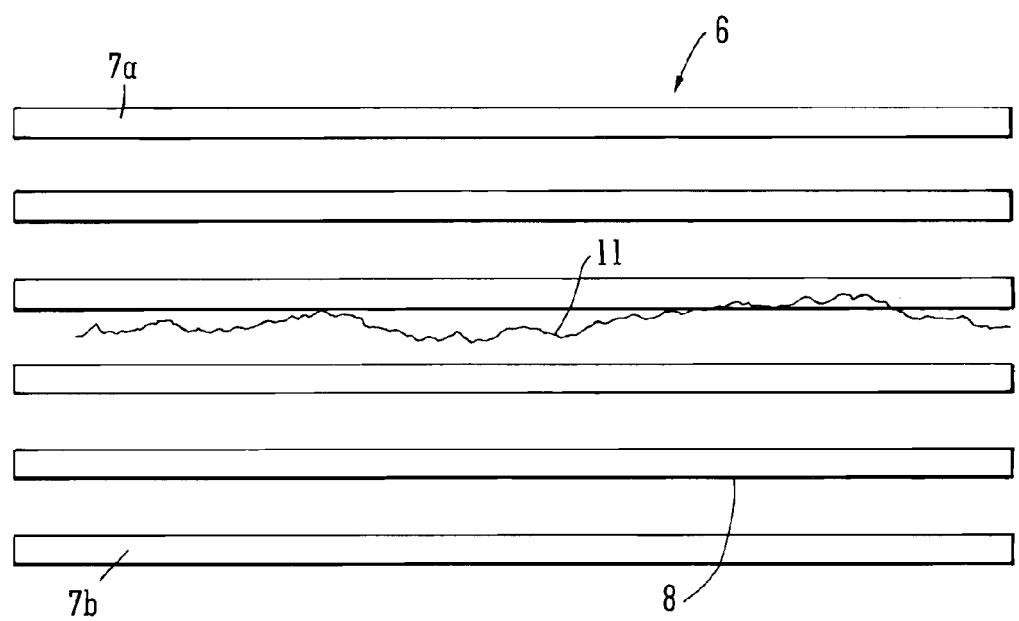
FIG. 5 shows a view of the trajectory of an ion along the length of the device when the device was operated in an ion guiding only mode of operation.

FIG. 5 shows the results of a simulation wherein an ion having a mass to charge ratio of 500 was modeled as passing through the device 6 shown in FIG. 4 but wherein the device 6 was arranged to operate in an ion guiding only mode of operation. According to this mode of operation an asymmetric voltage waveform was not applied to the upper electrode 7a and hence ions were not therefore arranged to be separated according to differences in their ion mobility with electric field strength.

In the various simulations which were performed the intermediate electrodes 8 were modeled as being supplied with an RF voltage having a frequency of 1 MHz and an amplitude of 200 V peak-peak. In the ion guiding only mode of operation the upper electrode 7a and the lower electrode 7b were both modeled as being maintained at 0V DC.

The preferred device 6 was further modeled as being subjected to a simulated gas pressure of 1 mbar of Argon (350 m/s thermal velocity, 1.64 $Å^3$ polarizability). The ion-neutral hard-sphere interaction cross section was modeled as being 200 $Å^2$ and a neutral gas bulk-flow velocity of 50 m/s was assumed.

Figure 6:
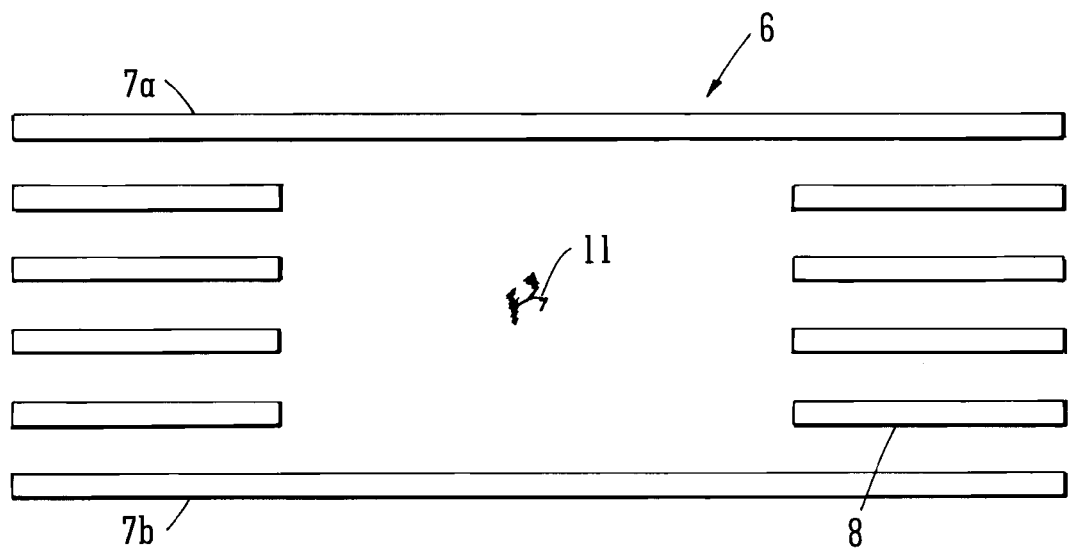
FIG. 6 shows an end-on view of the trajectory of the ion through the device when the device was operated in an ion guiding only mode of operation.

The trajectory 11 of the ion along the axial length of the device 6 operating in the ion guiding only mode of operation is shown in FIG. 5. FIG. 6 shows the trajectory of the same ion looking down the length of the device 6 i.e. looking in the z-direction. As will be appreciated from FIGS. 5 and 6, the ion is effectively transported along and through the length of the preferred device 6.

The effect of applying an asymmetric voltage waveform to the upper electrode 7a was then modeled. A SIMION® user program was used to model the effects of applying an asymmetric voltage waveform to the upper electrode 7a such that a high field voltage of 10*V was modeled as being applied to the upper electrode 7a for a period of time T. A low field voltage of −V was then modeled as being applied to the upper electrode 7a for a period of time 10*T. The lower electrode was meanwhile modeled as being maintained at 0V.

Figure 7:
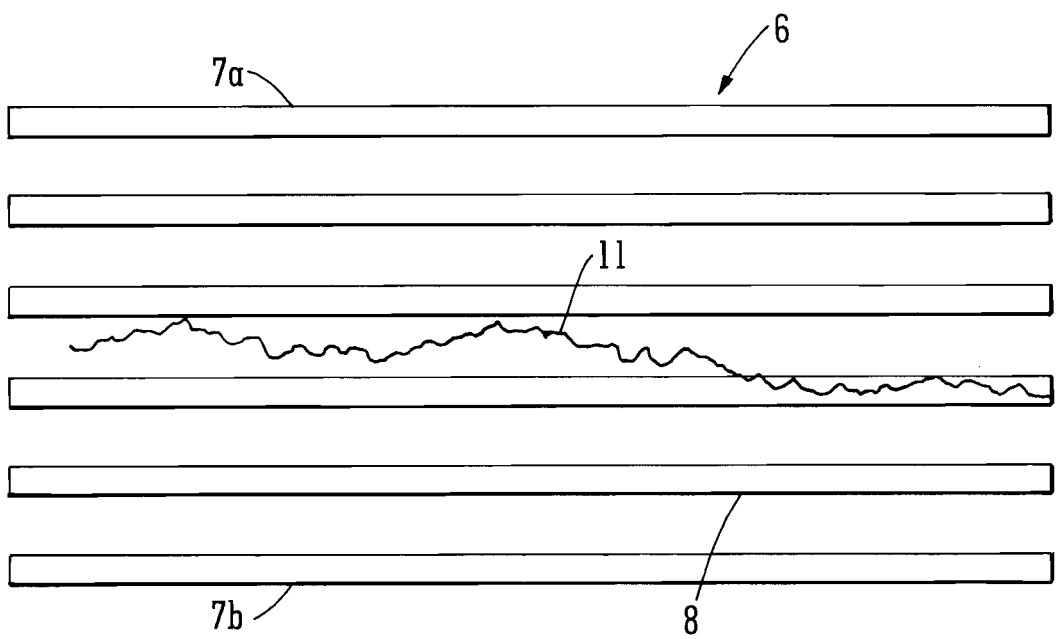
FIG. 7 shows how the trajectory of an ion is only mildly modulated when a relatively low amplitude asymmetric voltage waveform was applied to the upper electrode of the device.

FIG. 7 shows the result of a simulation wherein the parameter V was set to a relatively low value of 1 V and the parameter T was set to 1 μs. Accordingly, a high field voltage of only 10 V was applied to the upper electrode 7a for a time period 1 μs followed by a low field voltage of only −1 V being applied to the upper electrode 7a for a time period 10 μs. The other simulation parameters were kept the same as those used in the simulation described above in relation to FIGS. 5 and 6.

As can be seen from FIG. 7, the application of a relatively low amplitude asymmetric waveform to the upper electrode 7a had the effect of causing only a relatively small or minor degree of modulation to the trajectory 11 of the ion. It is also apparent that no particularly strong deviation of the ion to either the upper electrode 7a or to the lower electrode 7b was observed.

Figure 8:
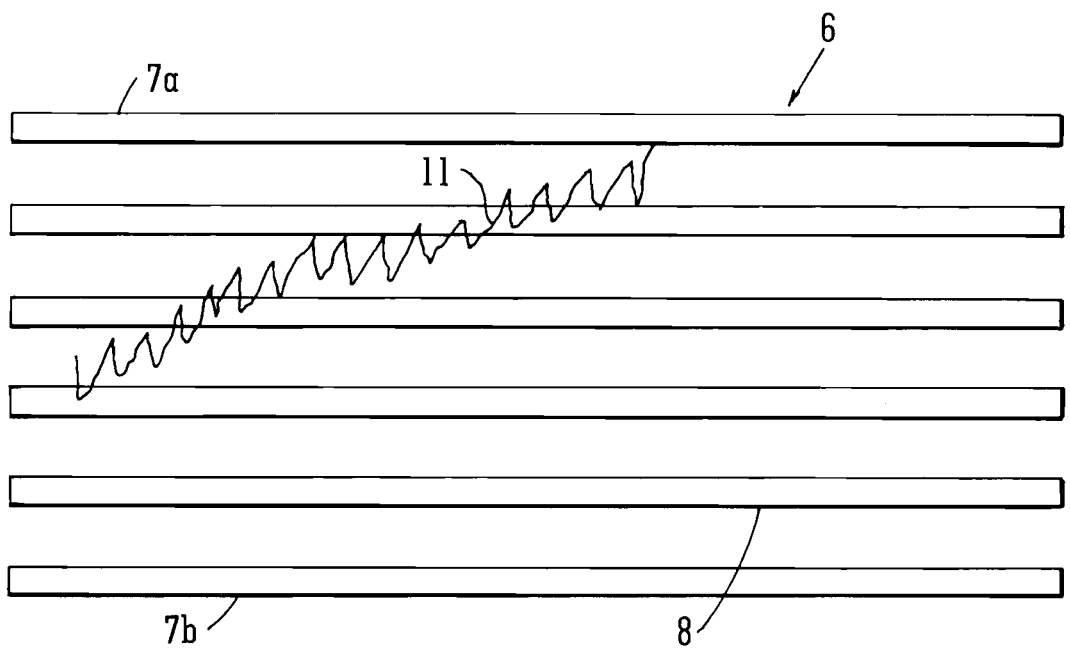
FIG. 8 shows how the trajectory of an ion passing through the device is strongly modulated when a high voltage asymmetric voltage waveform was applied to the upper electrode of the device.

FIG. 8 shows the result of a simulation wherein the voltage was increased such that the parameter V was now increased to 7 V. The parameter T was kept constant at 1 μs. Accordingly, a high field voltage of 70V was applied to the upper electrode 7a for a time period 1 μs and a low field voltage of −7 V was applied to the upper electrode 7a for a time period 10 μs. The other simulation parameters were kept the same as were used in respect of the simulation described above in relation to FIG. 7.

As is apparent from FIG. 8, when the amplitude of the asymmetric waveform was increased then a marked drift of the ion towards the upper electrode 7a was observed. This is due to the ion having a comparatively greater ion mobility under low electric field strength conditions (−7V) which meant that the ion is influenced to a greater extent during the longer low electric field portion of the applied asymmetric waveform.

As will now be discussed, the net or resultant drift of an ion towards either the upper electrode 7a or the lower electrode 7b can be compensated for by, for example, applying a compensating DC voltage to the lower electrode 7b.

Figure 9:
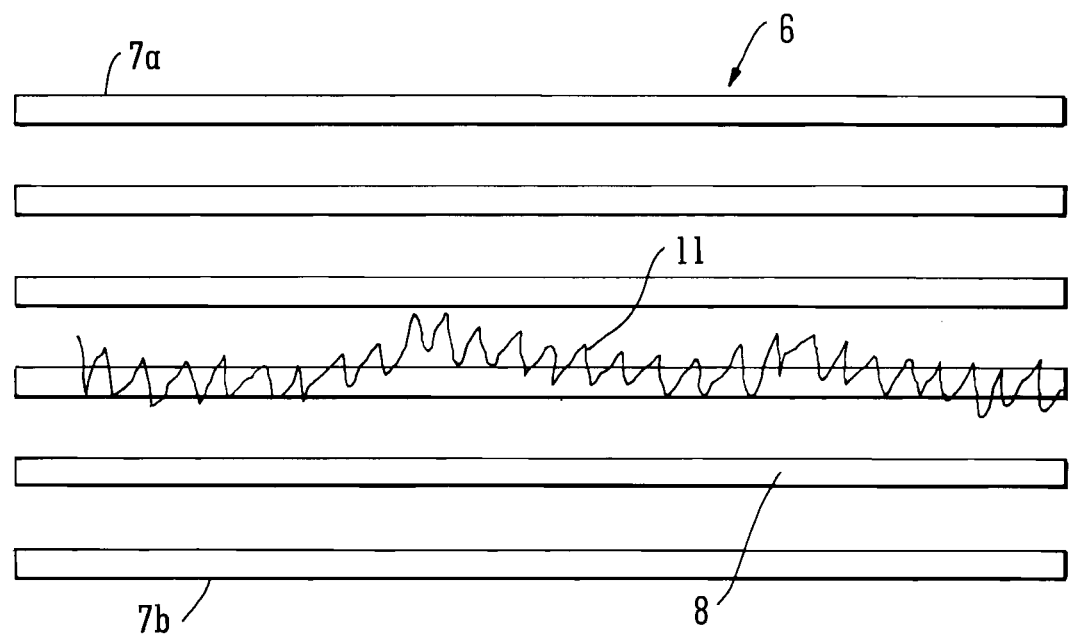
FIG. 9 shows the effect upon the trajectory of an ion by applying a DC compensation voltage to the lower electrode of the device in order to compensate for the differential mobility induced drift of the ion towards the upper electrode.

FIG. 9 shows the result of a simulation wherein the same asymmetric waveform as was applied in the simulation described above in relation to FIG. 8 was applied to the upper electrode 7a of the preferred device 6 and wherein also a compensating DC voltage of −1.5 V was applied to the lower electrode 7b. The applied DC compensating voltage can be seen as having the effect of effectively cancelling out the net drift of the ion towards the upper electrode 7a. The ion is therefore now observed to be onwardly transmitted along and through the device 6.

Figure 10:
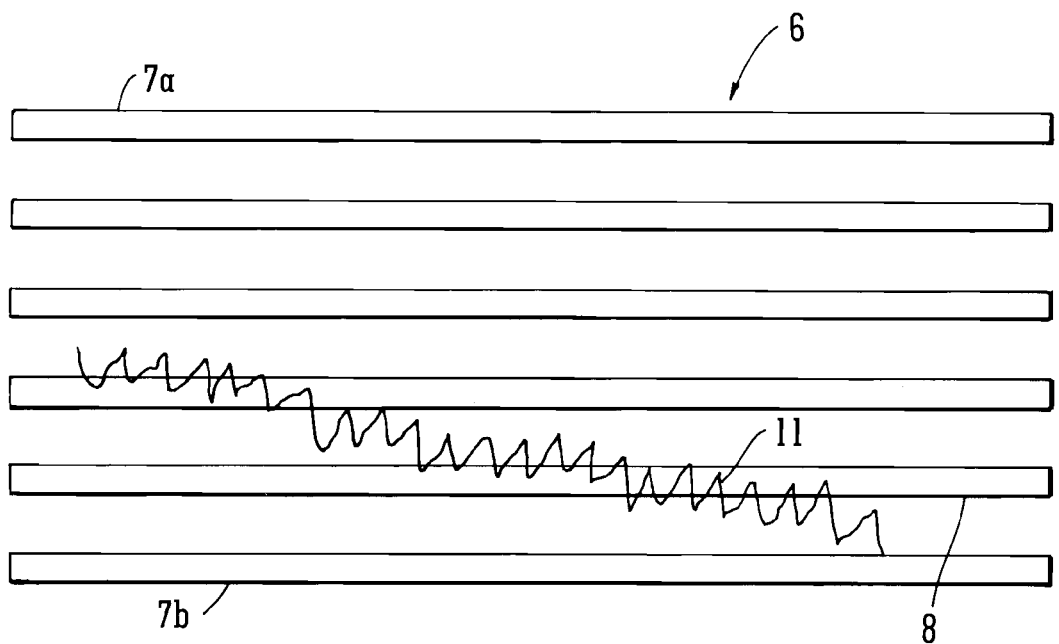
FIG. 10 shows the effect upon the trajectory of an ion if a DC compensation voltage is applied to the lower electrode which over compensates for the differential mobility induced drift of the ion towards the upper electrode.

FIG. 10 shows the result of a simulation wherein the compensating DC voltage applied to the lower electrode 7b was increased from −1.5 V to −2.0 V. It is apparent from FIG. 10 that the applied DC voltage now has the effect of over-correcting or over-compensating for the net drift of the ion towards the upper electrode 7a. The applied DC voltage actually causes the ion to drift now towards the opposite lower electrode 7b and ultimately to strike the lower electrode 7b.

Figure 11:
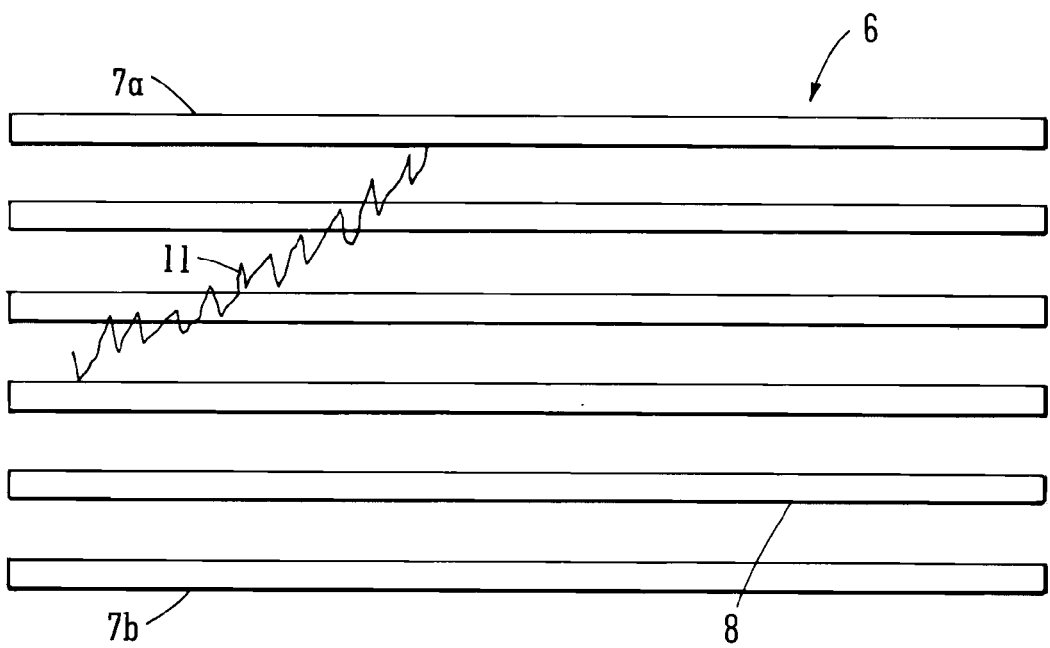
FIG. 11 shows the trajectory of an ion which was modeled as being subject to the same electric field conditions as described in relation to the embodiment described with reference to FIG. 8 but wherein the ion was modeled as having a larger cross-sectional area.

FIG. 11 shows the results of a simulation wherein the hard sphere interaction cross section used in the simulation model was increased from 200 to 300 Å$^2$. The parameter V was maintained at 7 V and the parameter T was maintained at 1 µs as with the simulations described above in relation to FIGS. 8-10. The asymmetric waveform was applied to the upper electrode 7a and the lower electrode 7b was maintained at 0 V DC.

It can be seen from comparing FIG. 11 with FIG. 8 that an ion having a larger cross-section will strike the upper electrode 7a sooner than an ion having a lower cross-section due to the ion having a reduced high field mobility if it has a larger interaction cross section.

Figure 12:
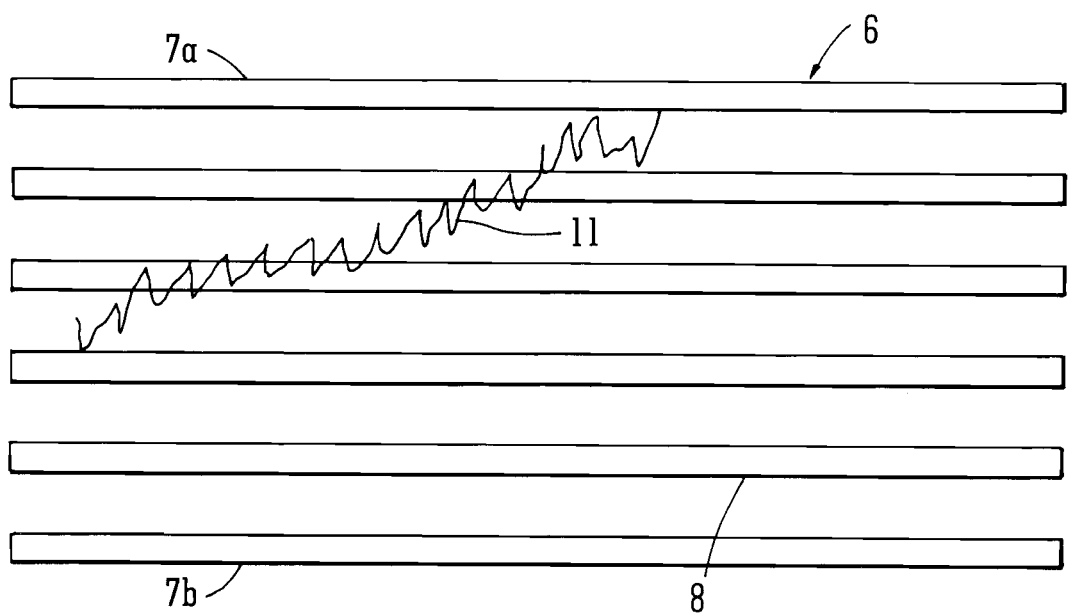
FIG. 12 shows that the trajectory of an ion towards the upper electrode is insufficiently compensated for if a DC compensation voltage having the same magnitude as the DC compensation voltage which as applied in the embodiment described with reference to FIG. 9 was applied to the lower electrode.

FIG. 12 shows the result of a simulation under the same conditions as for the simulation described and shown with relation to FIG. 11 except that a DC compensating voltage of −1.5 V DC was applied to the lower electrode 7b in a substantially similar manner to the simulation described above in relation to FIG. 9. However, it is apparent from FIG. 12 that the DC compensating voltage of −1.5 V was insufficient to compensate for the drift of the ion towards the upper electrode 7a and was therefore insufficient to prevent the ion from striking the upper electrode 7a.

Figure 13:
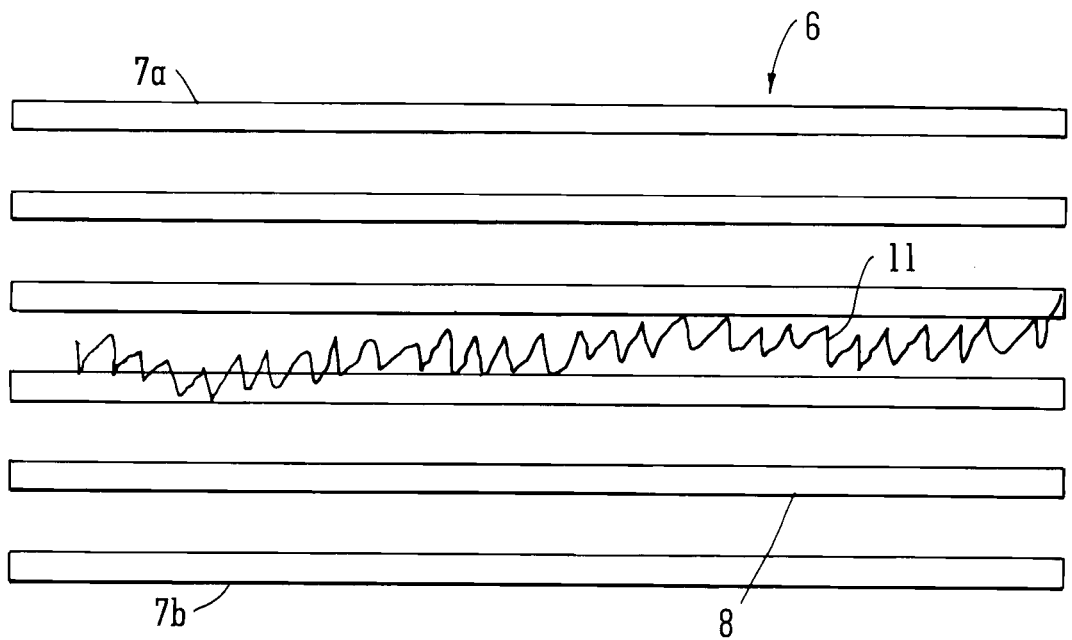
FIG. 13 shows how the trajectory of an ion may be modified or compensated for by applying the same magnitude DC compensation voltage which was applied in the embodiment described with reference to FIG. 10 to the lower electrode.

FIG. 13 shows the result of a simulation wherein the DC compensation voltage applied to the lower electrode 7b was increased from −1.5 V to −2 V. As can be seen from FIG. 13, increasing the DC compensation voltage to −2 V provided sufficient compensation for the net drift of the ion towards the upper electrode 7a such that the ion now passes along and through the preferred device 6 and is onwardly transmitted.

An ion mobility spectrum can be obtained by sweeping or progressively varying the DC compensating voltage which is applied to the lower electrode 7b. Alternatively, the DC compensating voltage applied to the lower electrode 7b may be kept substantially constant so that only ions having a certain desired mobility are then onwardly transmitted by the preferred device 6.

The gas which flows within and through the device 6 may be due to an inflow of gas through a differentially pumped vacuum stage. Alternatively, the preferred device 6 may be enclosed in a housing or envelope and a gas may be supplied to the housing or envelope in order to raise the gas pressure within the device 6 to an appropriate level. The housing or envelope may form a separate component of the mass spectrometer and may be contained or housed within a vacuum pumped chamber.

The ions entering the device 6 may come from an ionisation source and are entrained in a flow of gas. Alternatively, the ions may be created in a vacuum and/or may enter the device 6 from a vacuum chamber.

A mass spectrometer including the device 6 may include an Electrospray, Atmospheric Pressure Chemical Ionisation, Atmospheric Pressure Photoionisation, MALDI, Inductively Coupled Plasma, Electron Impact or Chemical Ionisation ion source. According to other embodiments other ion sources may alternatively be provided.

Ions exiting the device 6 may be detected directly by an ion detector. Alternatively, the ions exiting the device 6 may be subjected to further analysis prior to detection by an ion detector. It is contemplated, for example, that according to an embodiment of the present invention the ions exiting the device 6 may be subjected to mass spectrometric analysis, tandem mass spectrometry or further ion mobility spectrometry (or various combinations thereof).

The asymmetric waveform which is applied to the upper and/or lower electrodes 7a,7b preferably has a rectangular waveform. However, according to other embodiments the asymmetric waveform may have a waveform other than rectangular. For example, the waveform may be curved.

The transport of ions through the preferred device 6 in an axial direction (i.e. perpendicular to the mobility separation) was modeled in the embodiments shown and described above in relation to FIGS. 3-13 assuming that the gas flow velocity was kept.

According to an embodiment instead of using a gas flow to predominantly cause ions to continue moving in an axial direction through and along the preferred device 6, one or more axial electric fields may also or alternatively be used in order to drive, force, propel or urge ions along the axial direction of the device 6. Such an embodiment will be described now in more detail with reference to FIG. 14.

Figure 14:
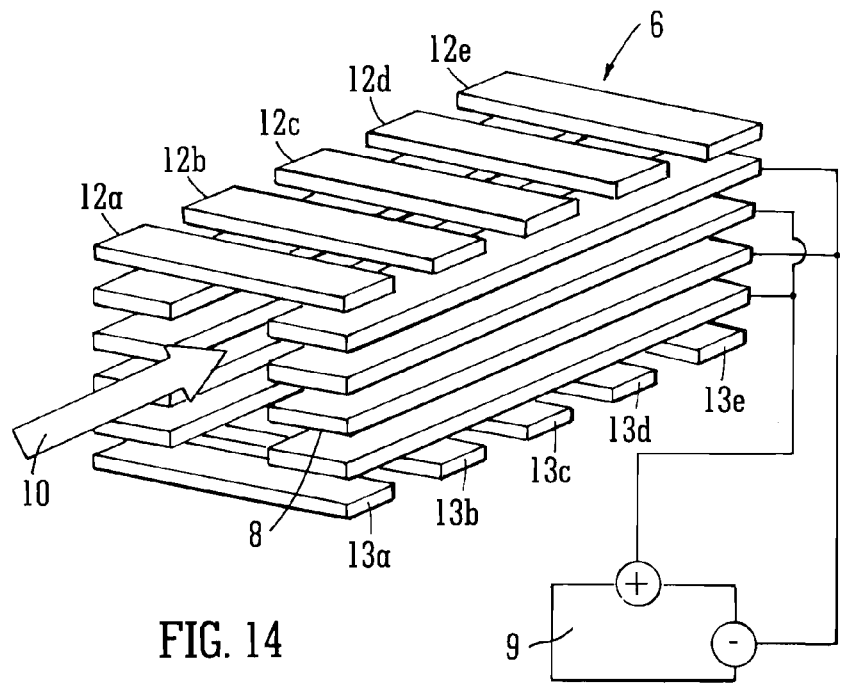
FIG. 14 shows a device wherein a plurality of axially segmented upper and lower electrodes are provided which enables a voltage gradient or a time varying voltage profile to be maintained along the axial length of the device in a mode of operation so that ions may be urged along and through the device.

According to this embodiment the upper electrode and/or the lower electrode of the preferred device 6 are axially segmented such that the upper electrode comprises an array of upper electrodes 12a-12e as shown in FIG. 14. Similarly, the lower electrode may also comprise an array of lower electrodes 13a-13e. The individual electrodes in the array of upper electrodes 12a-12e and the array of lower electrodes 13a-13e are electrically isolated from one another. The device 6 as shown in FIG. 14 comprises an array of upper electrodes 12a-12e, four intermediate layers 8 of longitudinal electrodes and an array of lower electrodes 13a-13e.

According to one embodiment a constant linear (or non-linear) voltage gradient may be provided along or maintained along at least a portion of the axial length of the preferred device 6 in the first and/or second modes of operation.

According to another embodiment ions may be axially driven, propelled or urged along at least a portion of the axial length of the preferred device 6 by applying one or more transient DC voltages or potentials or one or more DC voltage or potential waveforms to the first array electrodes 12a-12e and/or to the second array of electrodes 13a-13e in a mode of operation. The one or more transient DC voltages or potentials or one or more DC voltage or potential waveforms are preferably progressively applied to the array of upper electrodes 12a-12e and/or to the array of lower electrodes 13a-13e. The application of one or more transient DC voltages or potentials to the array of upper electrodes 12a-12e and/or to the array of lower electrodes 13a-13e preferably causes an electric field to be generated which ions can surf or otherwise be propelled or urged along the length of the preferred device 6 by.

Figure 15:
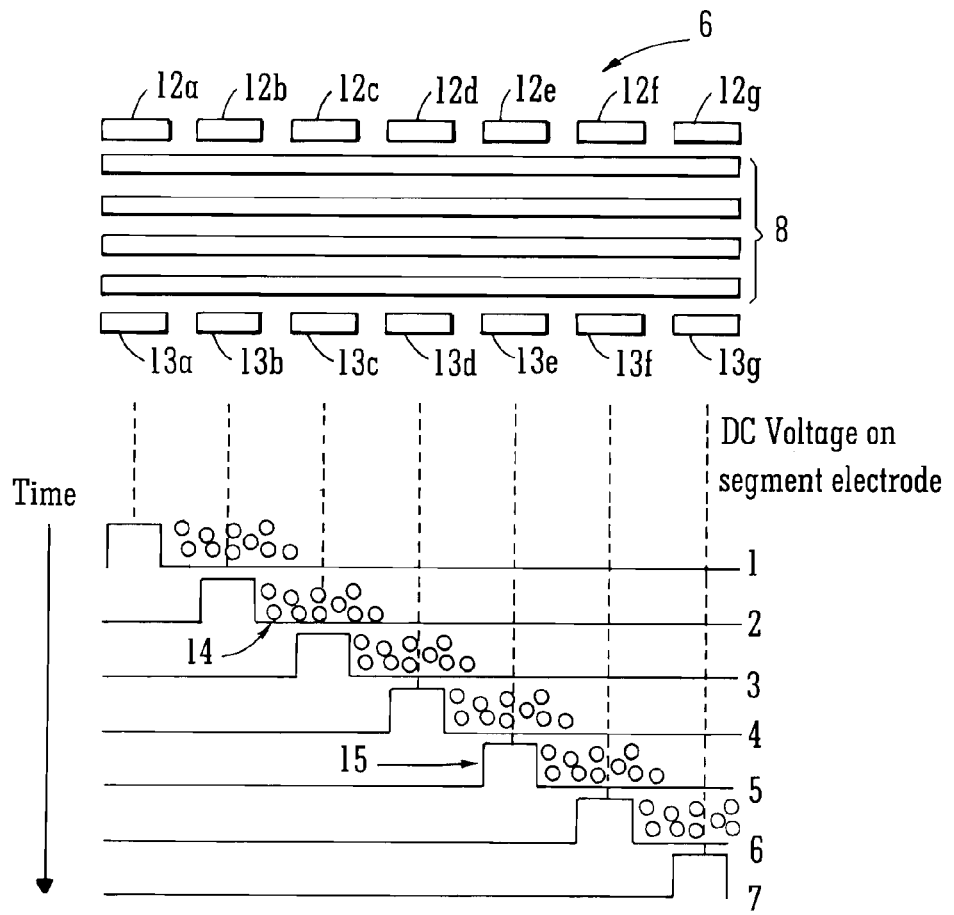
FIG. 15 shows a transient DC voltage or potential being progressively applied to the axially segmented upper and lower electrodes in order to urge ions along and through the device.

FIG. 15 shows a further embodiment comprising an array of seven upper electrodes 12a-12g, four intermediate layers 8 of electrodes and an array of seven lower electrodes 13a-13g. A transient DC voltage or potential is shown as being initially applied at a first time to a pair of first upper and lower electrodes 12a,13a. At a second later time the transient DC voltage is then applied to a pair of second upper and lower electrodes 12b,13b which are located downstream of the first upper and lower electrodes 12a,13a. The transient DC voltage is then progressively applied to subsequent pairs of electrodes e.g. to a pair of third upper and lower electrodes 12c,13c, then to a pair of fourth upper and lower electrodes 12d,13d, then a pair of fifth upper and lower electrodes 12e,13e, then a pair of sixth upper and lower electrodes 12f,13f before finally being applied to a pair of seventh upper and lower electrodes 12g,13g.

The application of one or more transient DC voltages or potentials or one or more transient DC voltage or potential waveforms to the array of upper electrodes 12a-12g and to the array of lower electrodes 13a-13g is such as to cause a series of axial potential wells to be formed or created within the preferred device 6. The axial potential wells are then translated or otherwise moved along the axial length of the preferred device 6. The application of one or more transient DC voltages or potentials or one or more transient DC voltage or potential waveforms enables the residence time of ions within the preferred device and hence in a region where they experience the effects of the orthogonally applied asymmetric field to be carefully controlled. This is a particularly advantageous feature of the preferred embodiment and enables the degree of ion mobility separation to be carefully controlled.

According to an embodiment of the present invention the velocity at which one or more axial potential wells are translated along the length of the preferred device 6 can be varied or even temporarily stopped.

The ion transport volume within the preferred device 6 has a substantially rectangular cross-section. However, other embodiments of the present invention are contemplated wherein the ion transport volume may have a cross-sectional form which is substantially non-rectangular. For example, it is contemplated that the cross-sectional form of the ion transport volume may vary along the axial length of the preferred device 6.

According to the preferred embodiment the ion confining volume within the preferred device 6 is linear. However, according to other embodiments the preferred device 6 may have a non-linear or serpentine ion guiding path or region. A non-linear or serpentine ion guiding path or region may be provided in order to increase the overall length of the transport volume and, for example, to improve the differential separation of ions for a preferred device 6 having a certain given overall axial length.

Figure 16:
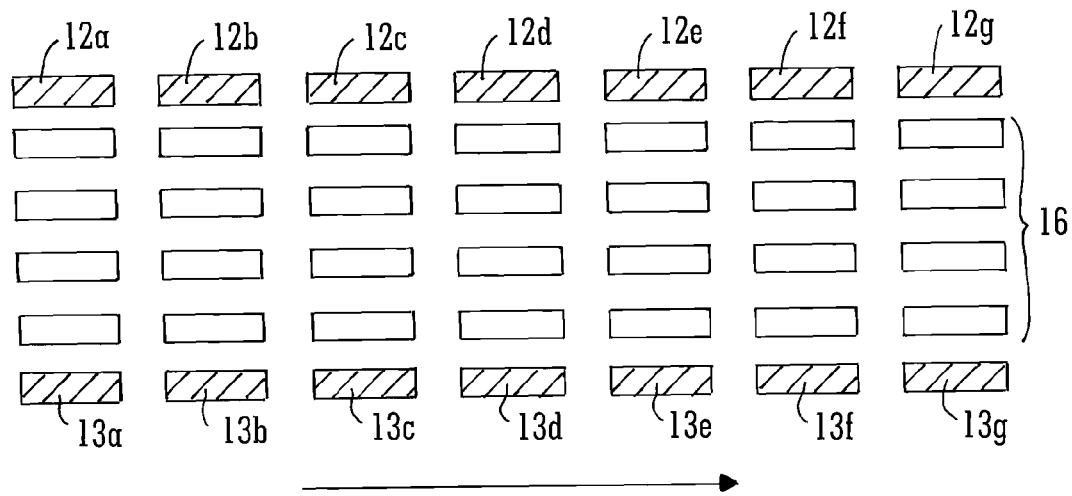
FIG. 16 shows a preferred embodiment of the present invention wherein both the upper and lower electrodes and the intermediate electrodes are axially segmented.

FIG. 16 shows a particularly preferred embodiment wherein both the upper electrodes 12a-12g, the lower electrodes 13a-13g and also the intermediate electrodes 16 are axially segmented. According to this embodiment an asymmetric voltage waveform may be applied to the upper electrodes 12a-12g (and/or the lower electrodes 13a-13g) and a DC compensation voltage may be applied to the lower electrodes 13a-13g (and/or the upper electrodes 12a-12g). As a result, ions are preferably separated in a first radial (i.e. vertical) direction according to their rate of change of ion mobility with electric field strength. RF voltages are preferably applied to the intermediate electrodes 16 in order to confine ions in a second (i.e. horizontal) radial direction. At the same time that an asymmetric voltage is preferably applied to the upper electrodes 12a-12g, an axial DC voltage gradient may also be applied or maintained along the length of the device. According to an embodiment the DC voltages are preferably applied to the upper electrodes 12a-12g and/or the intermediate electrodes 16 and/or the lower electrodes 13a-13g. The axially segmented intermediate electrodes are particularly advantageous in that they enable a more uniform axial DC electric field to be generated.

For illustrative purposes only, the first upper electrode 12a, the first lower electrode 13a and the intermediate electrodes arranged between the first upper electrode 12a and the first lower electrode 13a may be maintained at a potential of 20V, the second upper electrode 12b, the second lower electrode 13b and the intermediate electrodes arranged between the second upper electrode 12b and the second lower electrode 13b may be maintained at a potential of 19V, the third upper electrode 12c, the third lower electrode 13c and the intermediate electrodes arranged between the third upper electrode 12c and the third lower electrode 13c may be maintained at a potential of 18V etc. As a result, a DC voltage gradient is preferably maintained along the length of the device.

According to embodiments of the present invention ions may be separated according to their ion mobility in the axial direction according to a number of different ways. As discussed above, an axial DC voltage gradient may be maintained along the length of the ion mobility analyser. Alternatively, one or more transient DC voltages or DC voltage waveforms having a relatively low amplitude may be applied to the electrodes and ions may effectively surf over the transient DC voltages as the DC voltages are translated along the length of the ion mobility analyser in a manner which is linked to the ion mobility of the ions. As a result, ions become separated temporally according to their ion mobility. According to another embodiment a symmetric voltage waveform may be applied to the upper electrodes 12a-12g and/or the lower electrodes 13a-13g.

Figure 17:
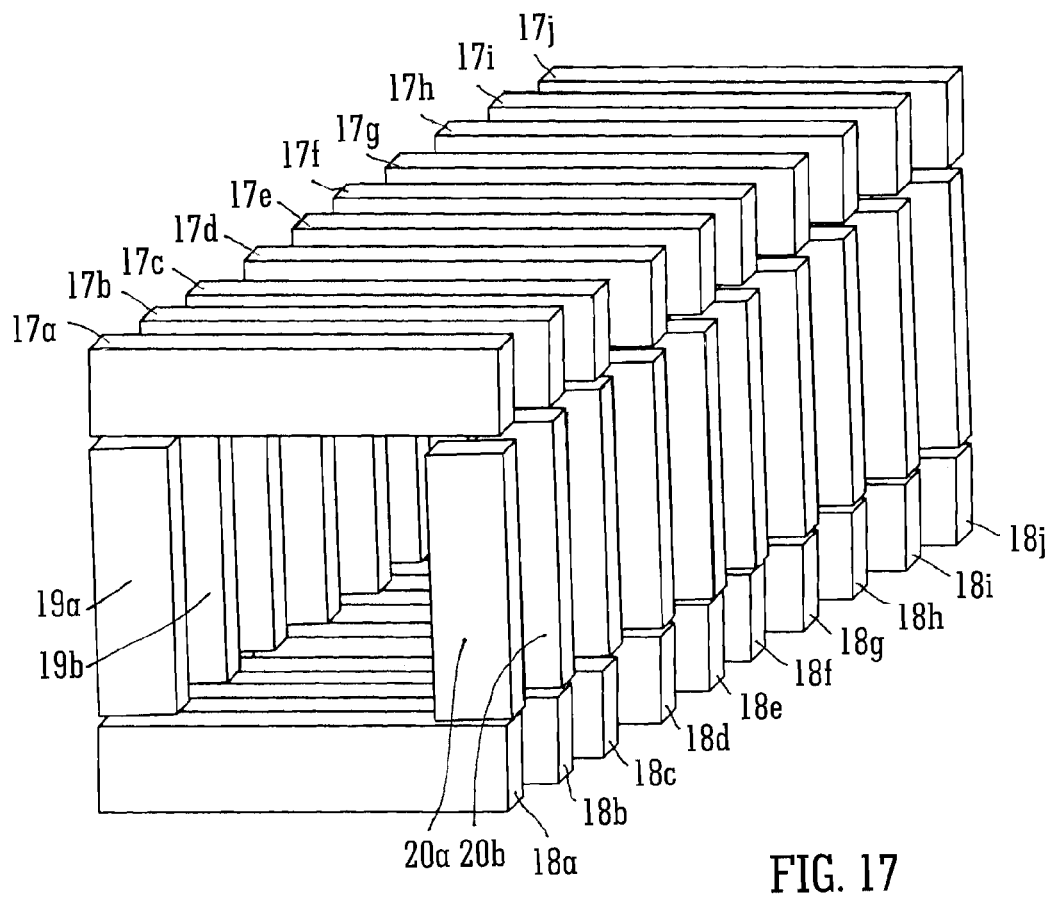
FIG. 17 shows an alternative embodiment of the present invention wherein the upper and lower electrodes and the intermediate electrodes are arranged in a ring stack type geometry.

FIG. 17 shows an alternative embodiment wherein the upper electrodes 17a-17g, the lower electrodes 18a-18j, the first intermediate electrodes 19a,19b . . . and the second intermediate electrodes 20a,20b . . . are arranged in a ring stack type geometry. According to this embodiment the electrodes are disposed linearly in a direction orthogonal to the ion pathway defined by the electrodes.

All the embodiments and different modes of operation discussed above may additionally be implemented using the ring stack arrangement of electrodes as shown in FIG. 17. For example, an ion-mobility analyser according to the embodiment shown in FIG. 17 may be provided wherein the ion-mobility analyser comprises a voltage source configured to apply simultaneously both: (i) an asymmetric voltage waveform to at least some of the electrodes so that ions become separated in a radial direction according to their rate of change of ion mobility with electric field strength; and (ii) a symmetric voltage to, one or more transient DC voltages to, or a linear axial voltage gradient across at least some of the electrodes so that ions become separated in an axial direction according to their ion mobility.

Although the present invention has been described with reference to preferred embodiments, it will be understood by those skilled in the art that various changes in form and detail may be made to the particular embodiments discussed above without departing from the scope of the invention as set forth in the accompanying claims.

The invention claimed is:
1. An ion-mobility analyser comprising:
an upper series of electrodes;
a lower series of electrodes disposed parallel to the upper series of electrodes;
a first plurality of intermediate electrodes disposed between the upper and lower series of electrodes;
a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;
a gas at a sub-ambient pressure in the ion pathway; and
a voltage source configured to apply simultaneously both:
(i) an asymmetric voltage waveform to at least some of said electrodes so that ions become separated in a radial direction according to their rate of change of ion mobility with electric field strength; and (ii) a symmetric voltage to, one or more transient DC voltages to, or a linear axial voltage gradient across at least some of said electrodes so that ions become separated in an axial direction according to their ion mobility.

2. An analyser as claimed in claim 1, wherein the analyser comprises a combined Field Asymmetric Ion Mobility Spectrometry-Ion Mobility Spectrometry ("FAIMS-IMS") device.

3. An analyser as claimed in claim 1, wherein the asymmetric voltage waveform comprises at least a first voltage component $V_{high}$ having a first peak amplitude and at least a second voltage component $V_{low}$ having a second peak amplitude substantially different from the first peak amplitude.

4. An analyser as claimed in claim 3, wherein said first voltage component is applied for a first time period $T_{high}$ and the second voltage component is applied for a second time period $T_{low}$ substantially different from said first time period.

5. An analyser as claimed in claim 1, further comprising a DC voltage source arranged and adapted to apply a DC compensation voltage to either the upper series of electrodes or to the first plurality of intermediate electrodes or to the second plurality of intermediate electrodes or to the lower electrodes.

6. An analyser as claimed in claim 1, wherein the upper series of electrodes, the lower series of electrodes, the first plurality of intermediate electrodes and the second plurality of intermediate electrodes are disposed linearly in a direction parallel to the ion pathway.

7. An analyser as claimed in claim 1, wherein the upper series of electrodes, the lower series of electrodes, the first plurality of intermediate electrodes and the second plurality of intermediate electrodes are disposed linearly in a direction orthogonal to the ion pathway.

8. A method of analysing ions comprising:
providing an ion-mobility analyser comprising an upper series of electrodes, a lower series of electrodes disposed parallel to the upper series of electrodes, a first plurality of intermediate electrodes disposed between the upper and lower series of electrodes, and a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;
providing a gas at a sub-ambient pressure in the ion pathway; and
applying simultaneously both: (i) an asymmetric voltage waveform to at least some of said electrodes so that ions become separated in a radial direction according to their rate of change of ion mobility with electric field strength; and (ii) a symmetric voltage to, one or more transient DC voltages to, or a linear axial voltage gradient across at least some of said electrodes so that ions become separated in an axial direction according to their ion mobility.

9. A multi-mode ion-mobility analyser comprising:
an upper series of electrodes;
a lower series of electrodes disposed parallel to the upper series of electrodes;
a first plurality of intermediate electrodes disposed between the upper and lower series of electrodes;
a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser;
a gas at a sub-ambient pressure in the ion pathway; and
a voltage source configured to apply a voltage waveform to at least some of the electrodes:
wherein in a first mode of operation either: (i) said voltage source applies simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) said voltage source applies an asymmetric voltage waveform to at least some of electrodes so that ions are separated radially according to their rate of change of ion mobility with electric field strength; or (iii) said voltage source applies a symmetric voltage waveform to, one or more transient DC voltages to, or a linear axial voltage gradient across at least some of electrodes so that ions are separated axially according to their ion mobility; and
wherein in a second different mode of operation either: (i) said voltage source applies simultaneously both an asymmetric waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) said voltage source applies an asymmetric voltage waveform to at least some of electrodes so that ions are separated radially according to their rate of change of ion mobility with electric field strength; (iii) said voltage source applies a symmetric voltage waveform to, one or more transient DC voltages to, or a linear axial voltage gradient across at least some of electrodes so that ions are separated axially according to their ion mobility; or (iv) ions are arranged to be transmitted through said analyser without being substantially separated either according to their rate of change of ion mobility with electric field strength or according to their ion mobility.

10. A method of analysing ions comprising:
providing a multi-mode ion-mobility analyser comprising an upper series of electrodes, a lower series of electrodes disposed parallel to the upper series of electrodes, a first plurality of intermediate electrodes disposed between the upper and lower series of electrodes, and a second plurality of intermediate electrodes disposed between the upper and lower series of electrodes and spaced from the first plurality of intermediate electrodes, wherein the upper and lower series of electrodes and the first and second plurality of intermediate electrodes define an ion pathway through which ions travel during operation of the analyser; and
providing a gas at a sub-ambient pressure in the ion pathway;
wherein in a first mode of operation the method further comprises either: (i) applying simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) applying an asymmetric voltage waveform to at least some of electrodes so that ions are separated radially according to their rate of change of ion mobility with electric field strength; or (iii) applying a symmetric voltage waveform to, one or more transient DC voltages to, or a linear axial voltage gradient across at least some of electrodes so that ions are separated axially according to their ion mobility; and wherein in a second different mode of operation said method further comprises either: (i) applying simultaneously both an asymmetric voltage waveform to at least some of electrodes so that ions are separated radially according to their rate of change of ion mobility with electric field strength and a symmetric voltage waveform to, one or more transient DC voltages to, or a linear axial voltage gradient across at least some of electrodes so that ions are separated axially according to their ion mobility; (ii) applying an asymmetric voltage waveform to at least some of electrodes so that ions are separated radially according to their rate of change of ion mobility with electric field strength; (iii) applying a symmetric voltage waveform to, one or more transient DC voltages to, or a linear axial voltage gradient across at least some of electrodes so that ions are separated axially according to their ion mobility; or (iv) arranging for ions to be transmitted through said analyser without being substantially separated either according to their rate of change of ion mobility with electric field strength or according to their ion mobility.

\* \* \* \* \*